US006537766B1

(12) United States Patent
Uckun et al.

(10) Patent No.: US 6,537,766 B1
(45) Date of Patent: Mar. 25, 2003

(54) IKAROS ISOFORMS AND MUTANTS

(75) Inventors: Fatih M. Uckun, White Bear Lake, MN (US); Mya L. Crotty, St. Paul, MN (US)

(73) Assignee: Hughes Institute, Roseville, MN (US)

( * ) Notice: Subject to any disclaimer, the term of this patent is extended or adjusted under 35 U.S.C. 154(b) by 0 days.

(21) Appl. No.: 09/435,327

(22) Filed: Nov. 5, 1999

Related U.S. Application Data
(60) Provisional application No. 60/107,229, filed on Nov. 5, 1998.

(51) Int. Cl.$^7$ .................. G01N 33/574; C12Q 1/00; C12Q 1/68; C12Q 33/53; C12Q 33/567
(52) U.S. Cl. .................. 435/7.23; 435/4; 435/6; 435/7.1; 435/7.21; 435/7.23; 435/7.24; 435/7.92; 435/7.25; 436/63; 436/64; 436/164; 436/166; 436/174; 436/501; 436/536; 530/300; 530/326; 530/328
(58) Field of Search .................. 435/4, 6, 7.1, 7.21, 435/7.92, 7.23, 7.24, 7.25; 436/536, 501, 166, 174, 63, 64, 164; 530/300, 328, 326

(56) References Cited

U.S. PATENT DOCUMENTS 5,824,770 A    10/1998   Georgopoulos

OTHER PUBLICATIONS

Hillier, L. et al., "Human cDNA Clone Image: 651072; IKAROS/LYF–1 Homologue", *EBML Sequence Database*, Abstract XP–002141591 (Feb. 22, 1997).

Nakayama, H. et al., "Aberrant IKAROS Expression in Human Nonlymphoid Leukemia Cell–Lines", *Blood*, vol. 88, No. 10, p. 3165, Abstract XP–000864665 (Nov. 15, 1996).

Nakayama, H. et al., "Dominant–Negative Mutants of Ikaros Gene in Human Lymphoid Leukemia Cell Lines", *Blood*, vol. 90, p. 493A, Abstract XP–000864669 (Nov. 15, 1996).

Sun, L. et al., "Expression of Aberrantly Spliced Oncogenic Ikaros Isoforms in Childhood Acute Lymphoblastic Leukemia", *Journal of Clinical Oncology*, vol. 17, No. 12, pp. 3753–3766, Abstract XP–000864666 (Dec. 1999).

Sun, L. et al., "Gene Mutations and Expression of Dominant–Negative IKAROS Isoforms in T–Cell Acute Lymphoblastic Leukemia", *Blood*, vol. 92, p. 152A, Abstract XP–00086468 (Nov. 15, 1998).

Uckun, F. et al., "IKAROS Gene Mutations and Expression of Dominant–Negative IKAROS Isoforms in Childhood Acute Lymphoblastic Leukemia", *PAACRA*, vol. 40, p. 282, Abstract XP–000914997 (Mar. 1999).

Arthur, D. et al., "Translocation 4; 11 in Acute Lymphoblastic Leukemia: Clinical Characteristics and Prognostic Significance", *Blood*, vol. 59, No. 1, pp. 96–99 (Jan. 1982).

Brown, K. et al., "Association of Transcriptionally Silent Genes with Ikaros Complexes at Centromeric Heterochromatin", *Cell*, vol. 91, No. 6, pp. 845–854 (Dec. 12, 1997).

Burnette, J. et al., "Trans–acting Factors Required for Inclusion of Regulated Exons in the Ultrabithorax mRNAs of *Drosophila melanogaster*", *Genetics*, vol. 151, No. 4, pp. 1517–1529 (Apr. 1999).

Chessells, J.M. et al., "Acute Lymphoblastic Leukaemia in Infancy: Experience in MRC UKALL Trials Report from the Medical Research Council Working Party on Childhood Leukaemia", *Leukemia*, vol. 8, No. 8, pp. 1275–1279 (Aug. 1994).

Coolidge, C. et al., "Functional Analysis of the Polypyrimidine Tract in pre–mRNA Splicing", *Nucleic Acid Research*, vol. 25, No. 4, pp. 888–895 (Feb. 15, 1997).

Côté, J. et al., "Natural Base–pairing Interactions Between 5' Splice Site and Branch Site Sequences Affect Mammalian 5' Splice Site Selection", *RNA*, vol. 3, No. 11, pp. 1248–1261 (Nov. 1997).

Crist, W. et al., "Clinical Features and Outcome in Childhood T–Cell Leukemia–Lymphoma According to Stage of Thymocyte Differentiation: A Pediatric Oncology Group Study", *Blood*, vol. 72, No. 6, pp. 1891–1897 (Dec. 1988).

Dignam, J. et al., Accurate Transcription Initiation by RNA Polymerase II in a Soluble Extract from Isolated Mammalian Nuclei, *Nucleic Acids Research*, vol. 11, No. 5, pp. 1475–1489 (1983).

Ford, A. et al., "In Utero Rearrangements in the Trithoraz–related Oncogene in Infant Leukaemias", *Nature*, vol. 363, No. 6427, pp. 358–360 (May 27, 1993).

Gale, K. et al., "Backtracking Leukemia to Birth: Identification of Clonotypic Gene Fusion Sequences in Neonatal Blood Spots", *Proc. Natl. Acad. Sci. USA*, vol. 94, No. 25, pp. 13950–13954 (Dec. 9, 1997).

Georgopoulos, K. et al., "Ikaros, an Early Lymphoid–Specific Transcription Factor and a Putative Mediator for T Cell Commitment", *Science*, vol. 258, pp. 808–812 (Oct. 30, 1992).

Georgopoulos, K. et al., "The Ikaros Gene is Required for the Development of all Lymphoid Lineages", *Cell*, vol. 79, pp. 143–156 (Oct. 7, 1994).

Georgopoulos, K. et al., "The Role of the Ikaros Gene in Lymphocyte Development and Homeostasis", *Annu. Rev. Immunol.*, vol. 15, pp. 155–176 (1997).

(List continued on next page.)

*Primary Examiner*—Yvonne Eyler
*Assistant Examiner*—Alana M. Harris
(74) *Attorney, Agent, or Firm*—Merchant & Gould P.C.

(57) ABSTRACT

Specific Ikaros mutations, as well as the correlation of the presence of the specific Ikaros mutations and other wild-type non-DNA binding Ikaros isoforms with lymphoid cell abnormality is provided in the in the invention. Methods for detecting and treating lymphoid cell abnormality, including hematoloic malignancy, are also provided.

4 Claims, 26 Drawing Sheets

OTHER PUBLICATIONS

Gill Super, H. et al., "Clonal, Nonconstitutional Rearrangements of the MLL Gene in Infant Twins with Acute Lymphoblastic Leukemia: In Utero Chromosome Rearrangement of 11q23", *Blood*, vol. 83, No. 3, pp. 641–644 (Feb. 1, 1994).

Greaves, M., "Differentiation–linked Leukemogenesis in Lymphocytes", *Science*, vol. 234, pp. 697–704 (Nov. 7, 1986).

Greaves, M.F., "Infant Leukaemia Biology, Aetiology and Treatment", *Leukemia*, vol. 10, No. 2, pp. 372–377 (Feb. 1996).

Hahm, K. et al., "The Lymphoid Transcription Factor LyF–1 is Encoded by Specific Alternatively Spliced mRNAs Derived from the Ikaros Gene", *Mol. Cell. Biol.*, vol. 14, No. 11, pp. 7111–7123 (Nov. 1994).

Hahm, K. et al., "Helios, a T Cell–restricted Ikaros Family Member that Quantitatively Associates with Ikaros at Centromeric Heterochromatin", *Genes & Development*, vol. 12, No. 6, pp. 782–796 (Mar. 15, 1998).

Hansen, J. et al., "Conservation of a Master Hematopoietic Switch Gene During Vertebrate Evolution: Isolation and Characterization of Ikaros from Teleost and Amphibian Species", *Eur. J. Immunol.*, vol. 27, No. 11, pp. 3049–3058 (Nov. 1997).

Harada, H. et al., "Accelerated Exon Skipping of IRF–1 mRNA in Human Myelodysplasia/Leukemia; a Possible Mechanism of Tumor Suppressor Inactivation", *Oncogene*, vol. 9, No. 11, pp. 3313–3320 (Nov. 1994).

Heerema, N. et al., "Karyotypic and Clinical Findings in a Consecutive Series of Children with Acute Lymphocytic Leukemia", *Cancer Genetics and Cytogenetics*, vol. 17, pp. 165–179 (1985).

Heerema, N. et al., "Cytogenetic Features of Infants Less than 12 Months of Age at Diagnosis of Acute Lymphoblastic Leukemia: Impact of the 11q23 Breakpoint on Outcome: A Report of the Childrens Cancer Group", *Blood*, vol. 83, No. 8, pp. 2274–2284 (Apr. 15, 1994).

Hunger, S. et al., "What Significance Should we Attribute to the Detection of MLL Fusion Transcripts?", *Blood*, vol. 92, No. 3, pp. 709–711 (Aug. 1, 1998).

Kelley, C. et al., "Helios, a Novel Dimerization Partner of Ikaros Expressed in the Earliest Hematopoietic Progenitors", *Current Biology*, vol. 8, No. 9, pp. 508–515 (Apr. 23, 1998).

Klug, C. et al., "Hematopoietic Stem Cells and Lymphoid Progenitors Express Different Ikaros Isoforms, and Ikaros is Localized to Heterochromatin in Immature Lymphocytes", *Proc. Natl. Acad. Sci. USA*, vol. 95, No. 2, pp. 657–662 (Jan. 20, 1998).

Köhler, G. et al., "Continuous Cultures of Fused Cells Secreting Antibody of Predifined Specificity", *Nature*, vol. 256, No. 5517, pp. 495–497 (Aug. 7, 1975).

Kristupaitis, D. et al., "Electromagnetic Field–induced Stimulation of Bruton's Tyrosine Kinase", *J. Biol. Chem.*, vol. 273, pp. 12397–12401 (1998).

Lopez, A., "Alternative Spicing of Pre–mRNA: Developmental Consequences and Mechanisms of Regulation", *Annu. Rev. Genet.*, vol. 32, pp. 279–305 (1998).

Luo, Z. et al., "Spicing of 5' Introns Dictates Alternative Splice Selection of Acetylcholinesterase Pre–mRNA and Specific Expression During Myogenesis", *J. Biol. Chem.*, vol. 273, No. 43, pp. 28486–28495 (Oct. 23, 1998).

McCarthy, E. et al., "Characterization of an Intron Splice Enhancer that Regulates Alternative Splicing of Human GH pre–mRNA", *Human Molecular Genetics*, vol. 7, No. 9, pp. 1491–1496 (Sep. 1998).

Molnár, A. et al., "The Ikaros Gene Encodes a Family of Functionally Diverse Zinc Finger DNA–Binding Proteins", *Mol. Cell Biol.*, vol. 14, No. 12, pp. 8292–8303 (Dec. 1994).

Molnár, A. et al., "The Ikaros Gene Encoded a Family of Lymphocyte–Restricted Zinc Finger DNA Binding Proteins, Highly Conserved in Human and Mouse", *J. Immunol.*, vol. 156, No. 2, pp. 585–592 (Jan. 15, 1996).

Morgan, B. et al., "Aiolos, a Lymphoid Restricted Transcription Factor that Interacts with Ikaros to Regulate Lymphocyte Differentiation", *The EMBO Journal*, vol. 16, No. 8, pp. 2004–2013 (Apjr. 15, 1997).

Nakayama, H., "Ikaros Gene Inactivation in Patients with Lymphoid Crisis of Chronic Myelogenous Leukemia", *Blood*, vol. 92, No. 10, Supplement 1 (Part 1 of 2), Abstract #909, (Nov. 15, 1998).

Poplack, D., "Acute Lymphoblastic Leukemia", *Prinicples and Practice of Pediatric Oncology*, Second Edition, Chapter 19, pp. 431–481 (1993).

Reaman, G. et al., "Treatment Outcome and Prognostic Factors for Infants with Acute Lymphoblastic Leukemia Treated on Two Consecutive Trials of the Children's Cancer Group", *J. Clin. Oncol.*, vol. 17, No. 2, pp. 445–455 (Feb. 1999).

Rubnitz, J. et al., "Molecular Genetics of Childhood Cancer: Implications for Pathogenesis, Diagnosis, and Treatment", *Pediatrics*, vol. 100, No. 1, pp. 101–108 (Jul. 1997).

Schaal, T. et al., "Multiple Distinct Splicing Enhancers in the Protein–Coding Sequences of a Constitutively Spliced Pre–mRNA", *Mol. Cell. Biol.*, vol. 19, No. 1, pp. 261–273 (Jan. 1999).

Schaal, T. et al., "Selection and Characterization of Pre–mRNA Splicing Enhancers: Identification of Novel SR Protein–Specific Enhancer Sequences", *Mol. Cell. Biol.*, vol. 19, No. 3, pp. 1705–1719 (Mar. 1999).

Smith, C. et al., "Mutually Exclusive Splicing of α–Tropomyosin Exons Enforced by an Unusual Lariat Branch Point Location: Implications for Constitutive Splicing", *Cell*, vol. 56, No. 5, pp. 749–758 (Mar. 10, 1989).

Smith, M. et al., "Uniform Approach to Risk Classification and Treatment Assignment for Children with Acute Lymphblastic Leukemia", *J. Clin. Oncol.*, vol. 14, No. 1, pp. 18–24 (Jan. 1996).

Sun, L. et al., "Zinc Finger–mediated Protein Interactions Modulate Ikaros Activity, a Molecular Control of Lymphocyte Development", *The EMBO Journal*, vol. 15, No. 19, pp. 5358–5369 (Oct. 1, 1996).

Sun, L. et al., "Expression of Dominant–negative and Mutant Isoforms of the Antileukemic Transcription Factor Ikaros in Infant Acute Lymphoblastic Leukemia", *Proc. Natl. Acad. Sci.USA*, vol. 96, pp. 680–685 (Jan. 1999).

Tamiya, S. et al., "Mutation of CD95 (Fas/Apo–1) Gene in Adult T–Cell Leukemia Cells", *Blood*, vol. 91, No. 10, pp. 3935–3942 (May 15, 1998).

Uckun, F. et al., "Biphenotypic Leukemic Lymphocyte Precursors in $CD2^+CD19^+$ Acute Lymphoblastic Leukemia and Their Putative Normal Counterparts in Human Fetal Hematopoietic Tissues", *Blood*, vol. 73, No. 4, pp. 1000–1015 (Mar. 1989).

Uckun, F. et al., "Interleukin 7 Receptor Ligation Stimulates Tyrosine Phosphorylation, Inositol Phospholipid Turnover, and Clonal Proliferation of Human B–cell Precursors", *Proc. Natl. Acad. Sci. USA*, vol. 88, No. 9, pp. 3589–3593 (May 1, 1991).

Uckun, F. et al., "Improved Clinical Outcome for Children with T–lineage Acute Lymphoblastic Leukemia After Contemporary Chemotherapy: A Children's Cancer Group Study", *Leukemia and Lymphoma*, vol. 24, pp. 57–70 (1996).

Uckun, F. et al., "BTK as a Mediator of Radiation–induced Apoptosis in DT–40 Lymphoma B Cells", *Science*, vol. 273, pp. 1096–1100 (Aug. 23, 1996).

Uckun, F. et al., "Clinical Features and Treatment Outcome of Childhood T–Lineage Acute Lymphoblastic Leukemia According to the Apparent Maturational Stage of T–Lineage Leukemic Blasts: A Children's Cancer Group Study", *J. Clinical Oncology*, vol. 15, No. 6, pp. 2214–2221 (Jun. 1997).

Uckun, F. et al., "Clinical Features and Treatment Outcome of Children with Myeloid Antigen Positive Acute Lymphoblastic Leukemia: A Report from the Children's Cancer Group", *Blood*, vol. 90, No. 1, pp. 28–35 (Jul. 1, 1997).

Uckun, F. et al., "Biology and Treatment of Childhood T–Lineage Acute Lymphoblastic Leukemia", *Blood*, vol. 91, No. 3, pp. 735–746 (Feb. 1, 1998).

Uckun, F. et al., "Cytotoxic Activity of Epidermal Growth Factor–Genistein against Breast Cancer Cells", *Clinical Cancer Research*, vol. 4, No. 4, pp. 901–912 (Apr. 1998).

Uckun, F. et al., "Clinical Significance of MLL–AF4 Fusion Transcript Expression in the Absence of a Cytogenetically Detectable t(4; 11) (q21; q23) Chromosomal Translocation", *Blood*, vol. 92, No. 3, pp. 810–821 (Aug. 1, 1998).

Wang, J. et al., "Selective Defects in the Development of the Fetal and Adult Lympoid System in Mice with an Ikaros Null Mutation", *Immunity*, vol. 5, No. 6, pp. 537–549 (Dec. 1996).

Winandy, S. et al., "A Dominant Mutation in the Ikaros Gene Leads to Rapid Development of Leukemia and Lymphoma", *Cell*, vol. 83, No. 2, pp. 289–299 (Oct. 20, 1995).

Fig. 1A2

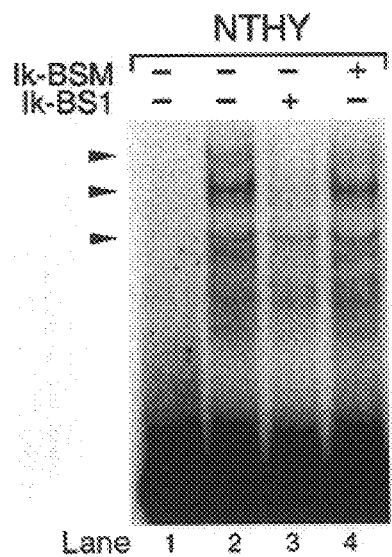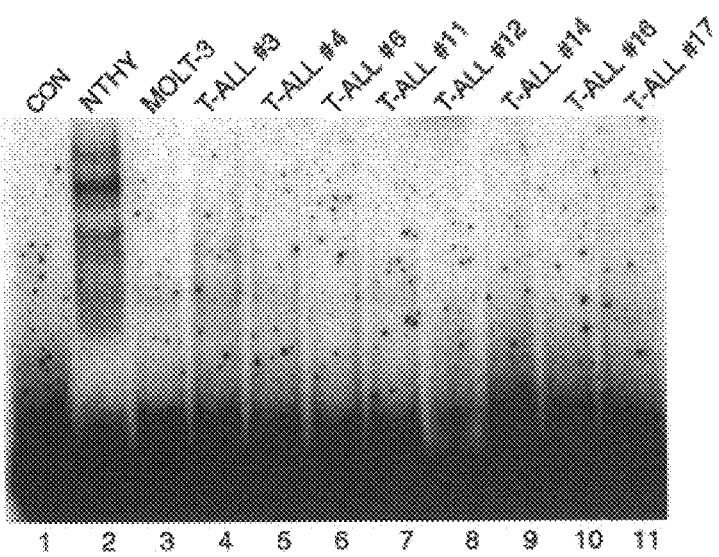
Fig. 3A
Fig. 3B

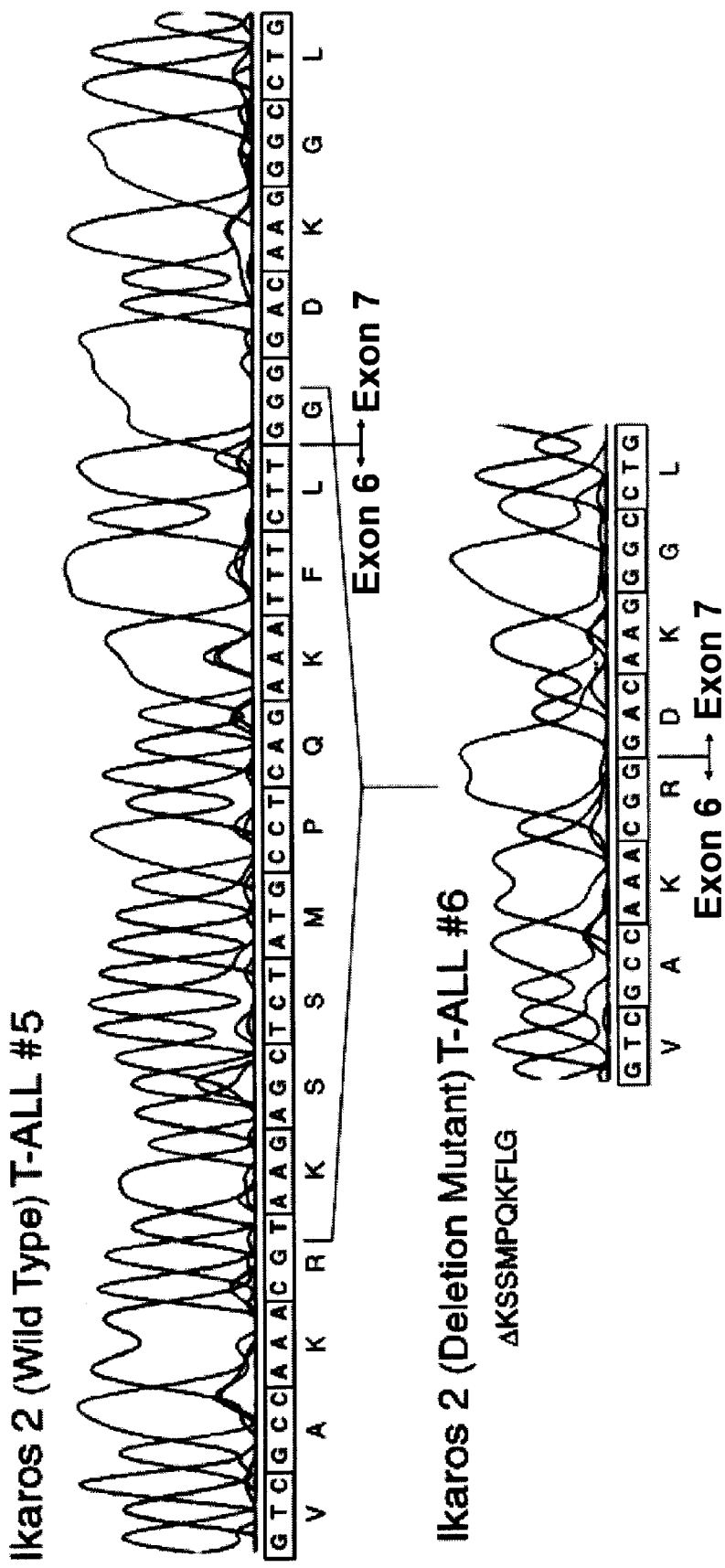

Fig. 9C

Expression Frequency of Ikaros 1002<sup>A</sup> and Ikaros 1002<sup>C</sup> Alleles

| PCR Clone | 1002 Allele | |
|---|---|---|
| | C | A |
| DNA binding isoforms [WT] | 26/33 (79) | 7/33 (21) |
| DNA binding isoforms [Δ KSSMPQKFLG] | 8/19 (42) | 11/19 (58) |
| Non-DNA binding isoforms [WT] | 22/29 (76) | 7/29 (24) |
| Non-DNA binding isoforms [Δ KSSMPQKFLG] | 43/47 (91) | 4/47 (9) |
| All Clones | 99/128 (77) | 29/128 (23) |

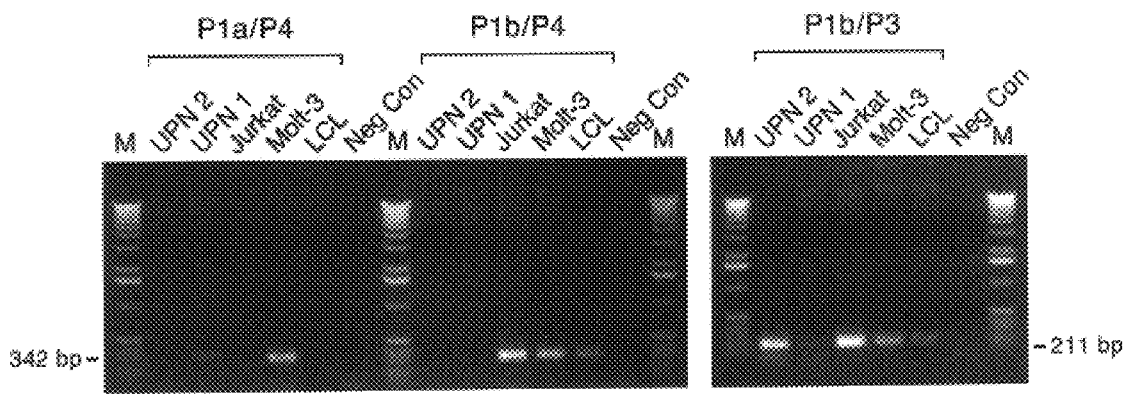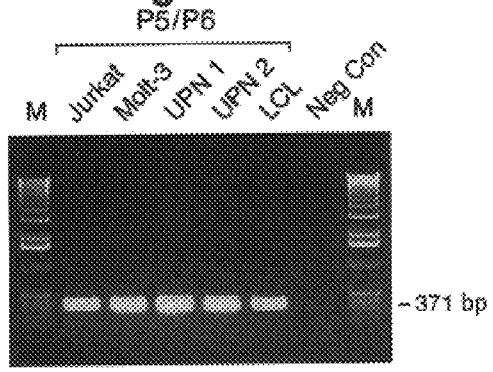

Fig. 12A

3'-INTRON 6

INTRON 6

DraI
attaatgaaatacaataattaaactaattttgttcccctattttatgtattcatttattccaacaaatctccttaagtgcttataatgggtaggtcctggctcggtgtccctggtgtccctggcagacgcatgggccttccc
SspI

P5 ccagccgtcagtggtgcaggtgtgatgtgtcgcaggtgtgtgtgtatgtgtcgcaggtgtggggtccgcaggcgtgttccctttccctcccccggttgtagatttcgctgtcgtcgtgctgccag

EXON 7

Branch
Point
Polypyrimidine Tract
acctgaccggttccgagggtggccgcgcccactcactgtcgctgctttccocagGGACAAGGGCTGTCCGACACGCCCAGCTACGACAGCAGCGCCAGCTACGAGAAGGAGAACGAAATGATGAAGTCCCACGTGATGAC
Splice
Acceptor

CAAGCCATCAACAACGCCATCAACTACCTGGGGGCCGAGTCCCCTGCGCCCGCT

P6       P7

SEQUENCE LISTING

```
<160> NUMBER OF SEQ ID NOS: 27

<210> SEQ ID NO 1
<211> LENGTH: 6
<212> TYPE: DNA
<213> ORGANISM: Homo sapiens

<400> SEQUENCE: 1 gggaat                                                                    6

<210> SEQ ID NO 2
<211> LENGTH: 24
<212> TYPE: DNA
<213> ORGANISM: Homo sapiens

<400> SEQUENCE: 2
tcagcttttg ggaataccct gtca                                               24

<210> SEQ ID NO 3
<211> LENGTH: 24
<212> TYPE: DNA
<213> ORGANISM: Homo sapiens

<400> SEQUENCE: 3
tcagcttttg ggggtaccct gtca                                               24

<210> SEQ ID NO 4
<211> LENGTH: 24
<212> TYPE: DNA
<213> ORGANISM: Homo sapiens

<400> SEQUENCE: 4
atggatgctg acgagggtca agac                                               24

<210> SEQ ID NO 5
<211> LENGTH: 24
<212> TYPE: DNA
<213> ORGANISM: Homo sapiens

<400> SEQUENCE: 5
ttagctcatg tggaagcggt gctc                                               24

<210> SEQ ID NO 6
<211> LENGTH: 20
<212> TYPE: DNA
<213> ORGANISM: Homo sapiens

<400> SEQUENCE: 6
ctcatcaggg aaggaaagcc                                                    20

<210> SEQ ID NO 7
<211> LENGTH: 22
<212> TYPE: DNA
<213> ORGANISM: Homo sapiens

<400> SEQUENCE: 7
ggtgtacatg acgtgatcca gg                                                 22

<210> SEQ ID NO 8
<211> LENGTH: 25
<212> TYPE: DNA
<213> ORGANISM: Homo sapiens
```

<400> SEQUENCE: 8
ttcagcggcc agtagcatct gactt                                    25

<210> SEQ ID NO 9
<211> LENGTH: 25
<212> TYPE: DNA
<213> ORGANISM: Homo sapiens

<400> SEQUENCE: 9
tgtgattata gcctaagacc cggag                                    25

<210> SEQ ID NO 10
<211> LENGTH: 63
<212> TYPE: DNA
<213> ORGANISM: Homo sapiens

<400> SEQUENCE: 10
gttacatatg gggctgatga ctttagggat ttccatgcaa taattcccaa atctttctct     60
cga                                                            63

<210> SEQ ID NO 11
<211> LENGTH: 21
<212> TYPE: PRT
<213> ORGANISM: Homo sapiens

<400> SEQUENCE: 11

Val Thr Tyr Gly Ala Asp Asp Phe Arg Asp Phe His Ala Ile Ile Pro
 1               5                  10                  15

Lys Ser Phe Ser Arg
            20

<210> SEQ ID NO 12
<211> LENGTH: 30
<212> TYPE: DNA
<213> ORGANISM: Homo sapiens

<400> SEQUENCE: 12
taagagctct atgcctcaga aatttcttgg                               30

<210> SEQ ID NO 13
<211> LENGTH: 10
<212> TYPE: PRT
<213> ORGANISM: Homo sapiens

<400> SEQUENCE: 13

Lys Ser Ser Met Pro Gln Lys Phe Leu Gly
 1               5                  10

<210> SEQ ID NO 14
<211> LENGTH: 27
<212> TYPE: DNA
<213> ORGANISM: Homo sapiens

<400> SEQUENCE: 14
taatcacagt gaatggcaga agacctg                                  27

<210> SEQ ID NO 15
<211> LENGTH: 28
<212> TYPE: DNA
<213> ORGANISM: Homo sapiens

<400> SEQUENCE: 15

```
ggcagaagac ctgtgcaaga taggatca                                           28
```

```
<210> SEQ ID NO 16
<211> LENGTH: 17
<212> TYPE: DNA
<213> ORGANISM: Homo sapiens

<400> SEQUENCE: 16
agcgggcgca gggactc                                                       17

<210> SEQ ID NO 17
<211> LENGTH: 21
<212> TYPE: DNA
<213> ORGANISM: Homo sapiens

<400> SEQUENCE: 17
gactcggccc ccaggtagtt g                                                  21

<210> SEQ ID NO 18
<211> LENGTH: 3629
<212> TYPE: DNA
<213> ORGANISM: Homo sapiens
<220> FEATURE:
<221> NAME/KEY: unsure
<222> LOCATION: (3078)
<223> OTHER INFORMATION: Genbank HSU40462

<400> SEQUENCE: 18
gaattccggc gtcgcggacg catcccagtc tgggcgggac gctcggccgc ggcgaggcgg         60
gcaagcctgg cagggcagag ggagccccgg ctccgaggtt gctcttcgcc cccgaggatc        120
agtcttggcc ccaaagcgcg acgcacaaat ccacataacc tgaggaccat ggatgctgat       180
gagggtcaag acatgtccca agtttcaggg aaggaaagcc cccctgtaag cgatactcca       240
gatgagggcg atgagcccat gccgatcccc gaggacctct ccaccacctc gggaggacag       300
caaagctcca agagtgacag agtcgtggcc agtaatgtta agtagagac tcagagtgat        360 gaagagaatg ggcgtgcctg tgaaatgaat ggggaagaat gtgcggagga tttacgaatg       420
cttgatgcct cggagagaa atgaatggc tcccacaggg accaaggcag ctcggctttg         480
tcgggagttg gaggcattcg acttcctaac ggaaaactaa agtgtgatat ctgtgggatc       540
atttgcatcg ggcccaatgt gctcatggtt cacaaaagaa gccacactgg agaacggccc       600
ttccagtgca atcagtgcgg ggcctcattc acccagaagg gcaacctgct ccggcacatc       660
aagctgcatt ccggggagaa gcccttcaaa tgccacctct gcaactacgc ctgccgccgg       720
agggacgccc tcactggcca cctgaggacg cactccgttg gtaaacctca caatgtgga       780 tattgtggcc gaagctataa acagcgaagc tctttagagg aacataaaga gcgctgccac       840
aactacttgg aaagcatggg ccttccgggc acactgtacc cagtcattaa agaagaaact       900
aatcacagtg aaatggcaga agacctgtgc aagataggat cagagagatc tctcgtgctg       960
gacagactag caagtaacgt cgccaaacgt aagagctcta tgcctcagaa atttcttggg      1020
gacaagggcc tgtccgacac gccctacgac agcagcgcca gctacgagaa ggagaacgaa      1080
atgatgaagt cccacgtgat ggaccaagcc atcaacaacg ccatcaacta cctgggggcc      1140
gagtccctgc gcccgctggt gcagacgccc ccgggcggtt ccgaggtggt cccggtcatc      1200
agcccgatgt accagctgca caagccgctc gcggagggca cccgcgcctc caaccactcg      1260
gcccaggaca gcgccgtgga gaacctgctg ctgctctcca aggccaagtt ggtgcccctcg     1320
```

```
                                          -continued gagcgcgagg cgtccccgag caacagctgt caagactcca cggacaccga gagcaacaac    1380
gaggagcagc gcagcggtct catctacctg accaaccaca tcgccccgca cgcgcgcaac    1440
ggcttgtcgc tcaaggagga gcaccgcgcc tacgacctgc tgcgcgccgc ctccgagaac    1500
tcgcaggacg cgctccgcgt ggtcagcacc agcggggagc agatgaaggt gtacaagtgc    1560
gaacactgcc gggtgctctt cctggatcac gtcatgtaca ccatccacat gggctgccac    1620
ggcttccgtg atccttttga gtgcaacatg tgcggctacc acagccagga ccggtacgag    1680
ttctcgtcgc ataacgcg aggggagcac cgcttccaca tgagctaaag ccctcccgcg    1740 ccccacccc agaccccgag ccaccccagg aaaagcacaa ggactgccgc cttctcgctc    1800
ccgccagcag catagactgg actggaccag acaatgttgt gtttggattt gtaactgttt    1860 tttgttttt gtttgagttg gttgattggg gtttgatttg cttttgaaaa gatttttatt    1920
tttagaggca gggctgcatt gggagcatcc agaactgcta ccttcctaga tgtttcccca    1980
gacgctggct gagattccct cacctgtcgc ttcctagaat ccccttctcc aaacgattag    2040
tctaaatttt cagagagaaa tagataaaac acgccacagc ctgggaagga gcgtgctcta    2100
ccctgtgcta agcacggggt tcgcgcacca ggtgtctttt tccagtcccc agaagcagag    2160
agcacagccc ctgctgtgtg ggtctgcagg tgagcagaca ggacaggtgt gccgccaccc    2220
aagtgccaag acacagcagg gccaacaacc tgtgcccagg ccagcttcga gctacatgca    2280 tctaggcgg agaggctgca cttgtgagag aaaatactta tttcaagtca tattctgcgg    2340
taggaaaatg attgggttgg ggaaagtcgg tgtctgtcag actgccctgg gtggagggag    2400
acgccgggtt agagcctttg ggatcgtcct ggattcactg gcttggggga ggctgttcag    2460
atggcctgag cctcccgagg cttgctgccc cgtaggagga gactgtcttc ccgtgggcat    2520
atctggggag ccctgttccc cgcttttca ctcccatacc tttaatggcc cccaaaatct    2580
gtcactacaa tttaaacacc agtcccgaaa tttggatctt ctttcttttt gaatctctca    2640
aacggcaaca ttcctcagaa accaaagctt tatttcaaat ctcttccttc cctggctggt    2700
tccatctagt accagaggcc tcttttcctg aagaaatcca atcctagccc tcatttaat    2760 tatgtacatc tgtttgtagc cacaagcctg aatttctcag tgttggtaag tttcttaacc    2820
taccctcact atatattatt ctcgttttaa aacccataaa ggagtgattt agaacatcat    2880
taattttcca actcaatgaa atatgtgaa gcccagcatc tctgttgcta acacacagag    2940
ctcacctgtt gaaacccaag cttcaaaca tgttgaagct cttactgta aaggcaagcc    3000 agcatgtgtg tccacacata cataggatgg ctggctctgc acctgtagga tattggaatg    3060
cacagggcaa ttgagggnct gagccagacc ttcgagagt aatgccacca gatcccctag    3120
gaaagaggag gcaaatggca ctgcaggtga aaccccgcc catccgtgct atgacatgga    3180
ggcactgaag cccgaggaag gtgtgtggag attctaatcc caacaagcaa gggtctcctt    3240
caagattaat gctatcaatc attaaggtca ttactctcaa ccacctaggc aatgaagaat    3300
ataccatttc aaatatttac agtacttgtc ttcaccaaca ctgtcccaag gtgaaatgaa    3360
gcaacagaga ggaaattgta cataagtacc tcagcattta atccaaacag gggttcttag    3420
tctcagcact atgacatttt gggctgacta cttatttgtt aggcgggagc tctcctgtgc    3480
attgtaggat aattagcagt atccctggtg gctacccaat agacgccagt agcaccccga    3540
attgacaacc caaactctcc agacatcacc aactgtcccc tgcgaggaga aatcactcct    3600
gggggagaac cactgaccca aatgaattc                                     3629
```

<210> SEQ ID NO 19
<211> LENGTH: 1788
<212> TYPE: DNA
<213> ORGANISM: Homo sapiens

<400> SEQUENCE: 19

| | | | | | |
|---|---|---|---|---|---|
| agtgatttag | agtgcagtgt | ctggtatagg | tgtgtattct | tcccttttcg | gtctatgttc | 60 |
| tctcatttgt | attgtgtggg | gagaagtgac | ttttttttata | aaaagaaaaa | ggtatatgca | 120 |
| tcccagcaga | gaagcactgg | ctccacccag | tacctgcctc | ctcatgccac | cctctcaagc | 180 |
| caaaagccgg | gggaagccca | ggcaccttga | ccatgaccgc | ccgagactca | cacttctatg | 240 |
| gatgctgacg | agggtcaaga | catgtctttc | tcatcaggga | aggaaagccc | ccctgtaagc | 300 |
| gatactccag | atgagggcga | tgagcccatg | ccgatccccg | aggacctctc | caccacctcg | 360 |
| ggaggacagc | aaagctccaa | gagtgacaga | gtcgtggcca | gtaatgttaa | agtagagact | 420 |
| cagagtgatg | aagagaatgg | gcgtgcctgt | gaaatgaatg | gggaagaatg | tgcggaggat | 480 |
| ttacgaatgc | ttgatgcctc | gggagagaaa | atgaatggct | cccacaggga | ccaaggcagc | 540 |
| tcggctttgt | cgggagttgg | aggcattcga | cttcctaacg | gaaaactaaa | gtgtgatatc | 600 |
| tgtgggatca | tttgcatcgg | gcccaatgtg | ctcatggttc | acaaaagaag | ccacactgga | 660 |
| gaacggccct | tccagtgcaa | tcagtgcggg | gcctcattca | cccagaaggg | caacctgctc | 720 |
| cggcacatca | agctgcattc | cggggagaag | cccttcaaat | gccacctctg | caactacgcc | 780 |
| tgccgccgga | gggacgccct | cactggccac | ctgaggacgc | actccgttgg | taaacctcac | 840 |
| aaatgtggat | attgtggccg | aagctataaa | cagcgaacgt | ctttagagga | acataaagag | 900 |
| cgctgccaca | actacttgga | aagcatgggc | cttccgggca | cactgtaccc | agtcattaaa | 960 |
| gaagaaacta | agcacagtga | aatggcagaa | gacctgtgca | agataggatc | agagagatct | 1020 |
| ctcgtgctgg | acagactagc | aagtaatgtc | gccaaacgta | agagctctat | gcctcagaaa | 1080 |
| tttcttgggg | acaagggcct | gtccgacacg | ccctacgaca | gtgccacgta | cgagaaggag | 1140 |
| aacgaaatga | tgaagtccca | cgtgatggac | caagccatca | caacgccat | caactacctg | 1200 |
| ggggccgagt | ccctgcgccc | gctggtgcag | acgccccgg | gcggttccga | ggtggtcccg | 1260 |
| gtcatcagcc | cgatgtacca | gctgcacagg | cgctcggagg | gcaccccgcg | ctccaaccac | 1320 |
| tcggcccagg | acagcgccgt | ggagtacctg | ctgctgctct | ccaaggccaa | gttggtgccc | 1380 |
| tcggagcgcg | aggcgtcccc | gagcaacagc | tgccaagact | ccacggacac | cgagagcaac | 1440 |
| aacgaggagc | agcgcagcgg | tcttatctac | ctgaccaacc | acatcgcccg | acgcgcgcaa | 1500 |
| cgcgtgtcgc | tcaaggagga | gcaccgcgcc | tacgacctgc | tgcgcgccgc | ctccgagaac | 1560 |
| tcgcaggacg | cgctccgcgt | ggtcagcacc | agcggggagc | agatgaaggt | gtacaagtgc | 1620 |
| gaacactgcc | gggtgctctt | cctggatcac | gtcatgtaca | ccatccacat | gggctgccac | 1680 |
| ggcttccgtg | atccttttga | gtgcaacatg | tgcggctacc | acagccagga | ccggtacgag | 1740 |
| ttctcgtcgc | acataacgcg | agggagcac | cgcttccaca | tgagctaa | | 1788 |

<210> SEQ ID NO 20
<211> LENGTH: 28
<212> TYPE: DNA
<213> ORGANISM: Homo sapiens

<400> SEQUENCE: 20
taagcacagt gaaatggcag aagacctg                                        28

<210> SEQ ID NO 21

```
<211> LENGTH: 28
<212> TYPE: DNA
<213> ORGANISM: Homo sapiens

<400> SEQUENCE: 21
atgctgcaaa atcaaatcta ggaaaaac                                            28

<210> SEQ ID NO 22
<211> LENGTH: 27
<212> TYPE: DNA
<213> ORGANISM: Homo sapiens

<400> SEQUENCE: 22 tttcccttc ttccaccctc aactcat                                              27

<210> SEQ ID NO 23
<211> LENGTH: 22
<212> TYPE: DNA
<213> ORGANISM: Homo sapiens

<400> SEQUENCE: 23
gtaggtcctg gctcggtgtc cc                                                  22

<210> SEQ ID NO 24
<211> LENGTH: 467
<212> TYPE: DNA
<213> ORGANISM: Homo sapiens

<400> SEQUENCE: 24
attaaatgaa atacaataac ataattaaac taatctttgg ttccccctatt tatgtattca         60
tttatccaac aaaatctcct taagtgctta taatgggtag gtcctggctc ggtgtccccct       120
agacagacgc atgggccttc ccccagcccg tcagtatggt gcaggtgtga tgtgtccgca        180
ggtgtgtgtg tatgtgtgca ggtgtggggt ccgcaggcgt gctgggcccc caggccgtgt        240
tccccttccc ctccccggtt gtagatttca gctgttgctg ccagacctga ccggttccgg        300
aggtggccgc gccccactca ctgtcgcctg ctttccacag gggacaaggg cctgtccgac        360
acgccctacg acagcagcgc cagctacgag aaggagaacg aaatgatgaa gtcccacgtg        420
atggaccaag ccatcaacaa cgccatcaac tacctggggg ccgagtc                      467

<210> SEQ ID NO 25
<211> LENGTH: 373
<212> TYPE: DNA
<213> ORGANISM: Homo sapiens

<400> SEQUENCE: 25
taagcacagt gaaatggcag aagacctgtg caagatagga tcagagagat ctctcgtgct         60
ggacagacta gcaagtaacg tcgccaaacg taagagctct atgcctcaga aatttcttgg       120
taagagttaa atgtttgctg tctcttaaaa aaaaactatg tgggtgtttt agatgcaagt       180
agaaatgagt tgagggtgga agaaagggaa aaaaatctta ttttttcaaa aggaaaaatt       240
ggtaagctta acattcctta aatatcttag aattttttcc aataagtatc ttaaaaataa       300
caaacctccc atcagttttt cctagatttg attttgcagc atctggggcc tgccctgtga       360
tctgcctgtg gac                                                           373

<210> SEQ ID NO 26
<211> LENGTH: 24
<212> TYPE: DNA
<213> ORGANISM: Homo sapiens
```

```
<400> SEQUENCE: 26
ctcgccaaac gggacaaggg cctg                                          24

<210> SEQ ID NO 27
<211> LENGTH: 8
<212> TYPE: PRT
<213> ORGANISM: Homo sapiens

<400> SEQUENCE: 27

Val Ala Lys Arg Asp Lys Gly Leu
  1               5
```

IKAROS ISOFORMS AND MUTANTS

This application claims the benefit of U.S. Provisional Application Serial No. 60/107,229 filed Nov. 5, 1998, the disclosure of which is incorporated in its entirety.

FIELD OF THE INVENTION

This invention relates to wild-type isoforms and mutations of Ikaros, and to nucleic acid sequences encoding Ikaros, useful in the diagnosis and treatment of hematologic malignancy, particularly lymphoid malignancy, including stem cell leukemia and T-cell and B-cell acute lymphoblastic leukemia (ALL).

BACKGROUND OF THE INVENTION

Acute lymphoblastic leukemia (ALL) is the most common form of cancer in children Leukemic clones in ALL patients are thought to originate from normal lymphocyte precursors arrested at various stages of T- or B-lymphocyte development hence, any critical regulatory network that controls normal lymphocyte development is a potential target for a leukemogenic event.

One such regulatory network vital for normal lymphopoiesis involves Ikaros, a member of the Kruppel family "zinc finger" DNA-binding proteins. Ikaros acts as an evolutionarily conserved "master switch" of hematopoiesis that dictates the transcriptional regulation of the earliest stages of lymphocyte ontogeny and differentiation.[1] Programmed expression and function of the Ikaros gene is tightly controlled by alternative splicing of Ikaros pre-mRNA which results in production of eight different Ikaros isoforms. All eight Ikaros isoforms (Ik-1, Ik-2, Ik-3, Ik-4, Ik-5, Ik-6, Ik-7, and Ik-8) share a common carboxy(C)-terminal domain containing a transcription activation motif and two zinc finger motifs that are required for hetero- and homodimerization among the Ikaros isoforms and for interactions with other proteins.

[1] Georgopolous et al., 1994, *Cell*, 79:143–156; Georgopolous et al., 1992, *Science*, 258:808–812; Hahm et al., 1994, *Mol. Cell Biol.*, 14:7111–7123; Molnar and Georgopolous, 1994, *Mol. Cell Biol.*, 14: 8292–8303; Wang et al., 1996, *Immunity*, 5:537–549; Winandy et al., 1995, *Cell*, 83:289–299; Molnar et al., 1996, *J. of Immunol.*, 156:585–592; Sun et al., 1996, *EMBO J.*, 15:5358–5369; Hansen et al., 1997, *Eur. J. Immunol*, 27:3049–3058; Georgopolous et al., 1997, *Ann. Rev. Immunol.*, 15:155–176; Brown et al., 1997, *Cell*, 91:845–854; and Klug et al., 1998, *Proc. Natl. Acad. Sci. USA*, 95:657–662.

Only three of the eight Ikaros isoforms (Ik-1, Ik-2, and Ik-3), however, contain the requisite three or more amino (N)-terminal zinc fingers that confer high affinity binding to a Ikaros-specific core DNA sequence motif in the promoters of target genes[2]. The formation of homo- and heterodimers among the DNA binding isoforms increases their affinity for DNA, whereas heterodimers between the DNA binding isoforms (Ik-1, Ik-2, and Ik-3) and non-DNA binding isoforms (Ik-4, Ik-5, Ik-6, Ik-7, and Ik-8) are unable to bind DNA. Therefore, non-DNA-binding Ikaros proteins with fewer than three N-terminal zinc fingers can interfere with the activity of Ikaros isoforms that can bind DNA[3].

[2] Sun et al., 1996, *EMBO J.*, 15:5358–5369
[3] Molnar et al., 1996, *J. Immunol.*, 156:585–592; and Sun et al., 1996, *EMBO J.*, 15:5358–5369

In mice, absence of the normal Ikaros gene results in an early and complete arrest in the development of all lymphoid lineages during both fetal and adult hematopoiesis[4]. Ikaros-deficient mice have a rudimentary thymus, lack peripheral lymph nodes and are characterized by a complete absence of lymphocyte progenitor cells as well as mature B-lymphocytes, T-lymphocytes, and natural killer cells. Ikaros also has a very important leukemia suppressor function which depends on its DNA binding ability: Mice heterozygous for a germline mutation which results in loss of critical DNA-binding zinc fingers of Ikaros develop a very aggressive form of lymphoblastic leukemia with a concomitant loss of heterozygosity between three and six months after birth[5]. Moreover, Ikaros has been localized to centromeric heterochromatin in immature lymphocyte precursors and it has been proposed that Ikaros might play an important role in recruitment and centromere-associated silencing of potentially "leukemogenic" growth regulatory genes.[6]

[4] Georgopolous et al., 1994, *Cell*, 79:143–156
[5] Winandy et al., 1995, *Cell*, 83:289–299
[6] Brown et al., 1997, *Cell*, 91:845–854; and Klug et al., 1998, *Proc. Natl. Acad. Sci. USA*, 95:657–662

Specific molecular defects in the Ikaros gene and its encoded protein have not been previously identifed, nor has Ikaros or any of its isoforms been implicated in human disease. Determination of such defects and the correlation of the specific defect to human leukemic disease would provide particularly useful diagnostic and therapeutic tools.

SUMMARY OF THE INVENTION

The present invention provides diagnostic and therapeutic tools based on the discovery of a direct correlation of non-DNA-binding IKAROS isoforms and/or specific IKAROS gene mutations and mutant proteins with lymphoid disease, and particularly with cancer, such as leukemia. Specific Ikaros mutations resulting from splice variants which lead to an in-frame deletion of ten amino acids (ΔKSSMPQKFLG [SEQ ID NO: 13]) upstream of the transcription activation domain and adjacent to the carboxy-terminal zinc fingers have been identified in children and infants with acute lymphoblastic leukemia (ALL), expressing high levels of dysfunctional dominant-negative Ikaros isoforms. In addition, a second specific Ikaros mutation leading to an in-frame insertion of 20 amino acids TYGADDFRDFHAIIPKSFSR [SEQ ID NO: 11] has also been identified in leukemic cells.

The identification of these specific defects and their association with ALL, as well as the correlation of dominant-negative Ikaros isoforms with hematoloic malignancy, provide useful tools for the diagnosis and monitoring of cancer, and particularly hematologic malignancy, including lymphoid malignancy and lymphoma. Such diagnostic tools correlate the abundance of dominant-negative Ikaros isoforms (non-DNA-binding isoforms) and/or the presence of specific Ikaros mutations with hematologic cell abnormality, including malignancies. The correlation of these defects in Ikaros expression in abnormal cells, such as leukemic cells, also provides therapeutic tools for repairing the defect and restoring normal hematologic cell function.

Accordingly, the present invention provides nucleic acid and protein sequences of specific Ikaros mutations. The invention further provides methods for the analysis of Ikaros proteins and for discriminating between wild type and mutant forms, as well as between DNA-binding and non-binding isoforms.

Diagnostic methods of the invention correlate the abundance of non-DNA-binding forms of Ikaros, for example, present in a ratio >1, with disease, particularly with cancer. An abundance of non-DNA-binding isoforms and/or mutants correlates with lymphoid disease, and most particularly with leukemias, including AML, ALL, and secondary leukemias. Ikaros proteins, including isoforms and mutants, and nucleic acid sequences encoding them, can be analyzed by one or more methods described in the detailed description and examples below.

The present invention also provides for the replacement of DNA-binding forms of Ikaros in the treatment of disease, for example in the treatment of cancer such as leukemia, where DNA-binding forms are diminished or absent.

BRIEF DESCRIPTION OF THE DRAWINGS

FIGS. 1A.1 and 1A.2 show Ikaros protein expressed in Jurkat T-lineage ALL cells and normal fetal liver-derived human lymphocyte precursor cell lines FL8.2$^+$ and FL8.2$^-$. FIG. 1B shows Ikaros protein expressed in normal thymocytes (NTHY-5) and 6 different B-lineage ALL cell lines. FIG. 1C shows Ikaros proteins expressed in normal thymocytes (NTHY-4) and leukemic cells from 8 children with non-infant B-lineage ALL. FIG. 1D shows Ikaros proteins expressed in normal bone marrow cells (NBM-1), normal infant thymocytes (NTHY), and fetal thymocytes (FT). FIGS. 1E–1G show Ikaros proteins expressed in JK-E6-1 and MOLT-3 leukemic cell lines, normal bone marrow mononuclear cells (NBM-2), and leukemic cells from children with T-ALL.

FIGS. 2A–2K show leukemic cells from B-lineage ALL patients. FIGS. 2Q–2S show primary leukemic cells from T-ALL patients.

FIGS. 3A and 3B show Ikaros-specific DNA binding activity of nuclear proteins extracted from normal thymocytes (NTHY) and leukemic T cells of T-ALL patients and the cell line MOLT-3.

FIG. 6 shows the wild type Ik-2 cDNA sequence spanning the junction between exon 2 and exon 4 [SEQ ID NO: 27] and its corresponding derived amino acid sequence [SEQ ID NO: 28], as well as the Ik-2 insertion mutant cDNA sequence spanning the junction between exon 2 and exon 4 [SEQ ID NO: 29] and its corresponding derived amino acid sequence [SEQ ID NO: 30].

FIGS. 8A–8F are sequence tracings spanning the junction between exon 6 and exon 7 from leukemic cells expressing the wild-type Ikaros 2 isoform and those expressing the deletion mutant. FIGS. 8A–8C show sequence tracings of wild-type and deletion mutant Ikaros isoforms obtained from patients with T-ALL and the MOLT-3 cell line. FIGS. 8D–8F show sequence tracings of wild-type and deletion mutant Ikaros isoforms obtained from patients with B-ALL and the MOLT-3 cell line. Shown are the wild-type cDNA sequences spanning the junction between exon 6 and exon 7 for Ik-2 and deletion mutant, Ik-4, IK-8, and Ik-7 and their corresponding derived amino acid sequences.

FIG. 9A is a schematic diagram of the Ikaros cDNA. Zinc fingers are labeled F1–F6; Ikaros exons are labeled E1–E7; and PCR primers (arrows) are labeled F1 and F2 (forward) and R1 and R2 (reverse). The location of the single nucleotide polymorphism site (C or A at position 1002) in the bipartite activation domain is shown.

FIG. 9C shows sequencing data spanning the single nucleotide polymorphism site from seven RT-PCR clones in NALM-6 B-lineage ALL cells. The alternative A or C at position 1002 is underlined. Typing results and cDNA sequencing results are shown from two Ik4 (non-DNA binding isoform [WT]) clones, one Ik4+deletion (non-DNA binding isoform (ΔKSSMPQKFLG) clone, two Ik2 (DNA Binding isoform [WT]) clones and two Ik2+deletion (DNA binding isoform (ΔKSSMPQKFLG) clones. Also shown are the corresponding deduced amino acid sequences.

FIGS. 10A–10E show photographs of representative ethidium bromide stained gels revealing PCR products used to determine sequence covering the exon 6/7 splice junction as described in Example 4. FIG. 10A shows the nested PCR products generated by amplification of the exon 6 donor site region.

FIG. 10B shows the nested PCR product surrounding the exon 7 slice acceptor site.

FIG. 10C shows genomic PCR amplification products for the exon 6 donor site, using primer sets P1a and P4 or P1b and P4.

FIG. 10D shows genomic PCR amplification products for the exon 6 donor site obtained from control cells and primary leukemic cells.

FIG. 10E shows genomic PCR amplification products for the exon 7 acceptor site obtained from control cells and primary leukemic cells from patients. Negative control (Neg. Con.) was duplicate reactions without template (either library digest or genomic DNA sample). Positive control (Pos. Con.) was tissue-type plasminogen activator (tPA), nested primer set, AP2 and PCP2, with a predicted band at 1.5 kb.

FIG. 11A shows the wild-type sequence surrounding the exon 6 donor site and ending at an EcoRV site within the intron spanning exons 6 and 7. Location of PCR primers used to determine this sequence are indicated. Coding sequence is capitalized and the intronic sequence is in lower case. The two alternative splice donor sites (donor site 1 and donor site 2) are shown.

FIG. 11B shows the sequence alignment and identity of the Ikaros exon 6 donor sites in a control EBV-transformed B-lymphoblastoid cell line (LCL), two T-cell ALL cell lines, JURKAT and MOLT-3, and leukemic cells from two ALL patients, UPN 1 and UPN 2.

FIGS. 12A–12B depict the genomic sequence of the Ikaros exon 6–7 splice acceptor site in leukemic cells expressing aberrant Ikaros isoforms having the 30 base pair deletion in exon 6. FIG. 12A shows the wild-type sequence surrounding the exon 6 splice acceptor site and ending at overlapping DraI and SspI sites. The location of PCR primers (P5, P6, and P7) used to determine this sequence are indicated. The coding sequence is capitalized and non-coding sequence is in lower case.

FIG. 12B shows the sequence alignment and identity of the exon 6–7 splice acceptor sequence in a control EBV-transformed B-lymphoblastoid cell line, LCL, two T-cell ALL cell lines, JURKAT and MOLT-3, and leukemic cells from two ALL patients, UPN 1 and UPN 2.

DETAILED DESCRIPTION OF THE INVENTION

Figure 1A:
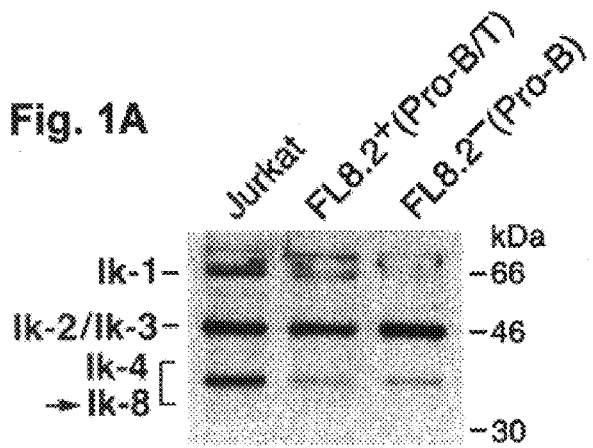
FIGS. 1A–1G are Western blots showing expression of Ikaros protein isoforms in normal and leukemia cells.
Figure 1B:
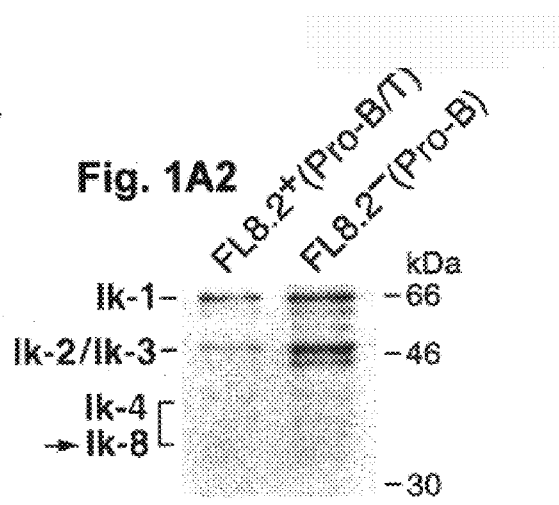
Figure 1B:
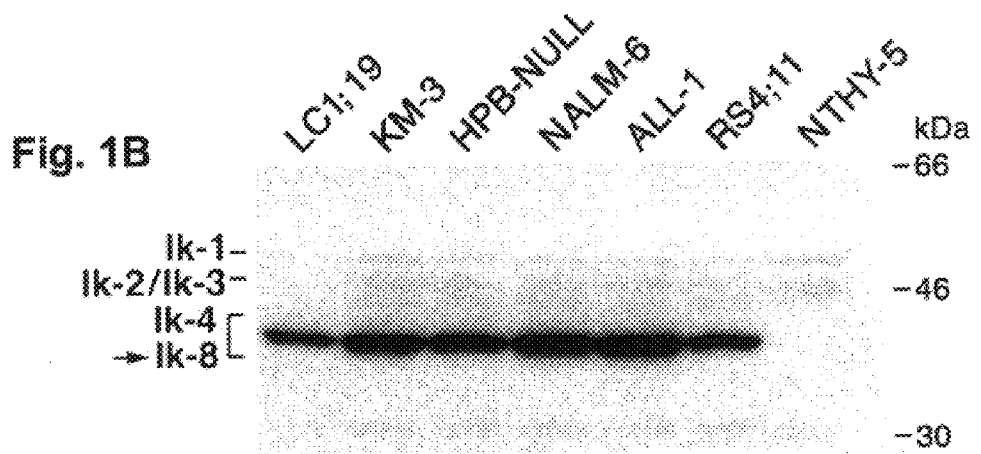
Figure 1C:
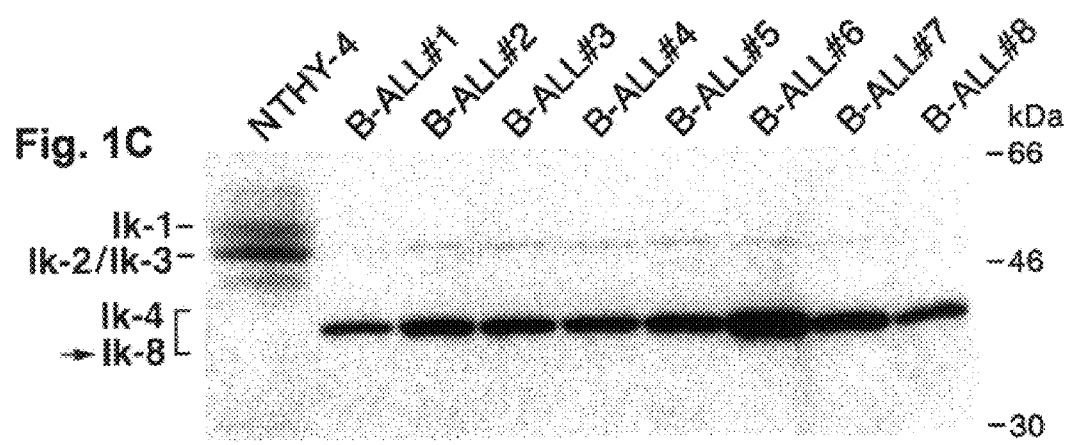
Figure 1D:
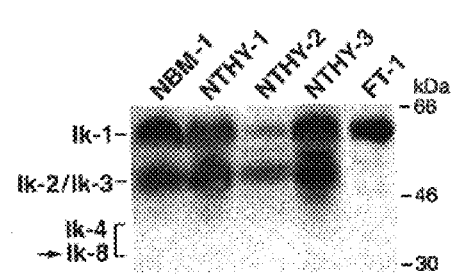
Figure 1E:
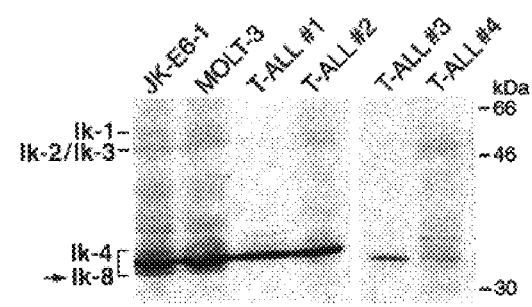
Figure 1F:
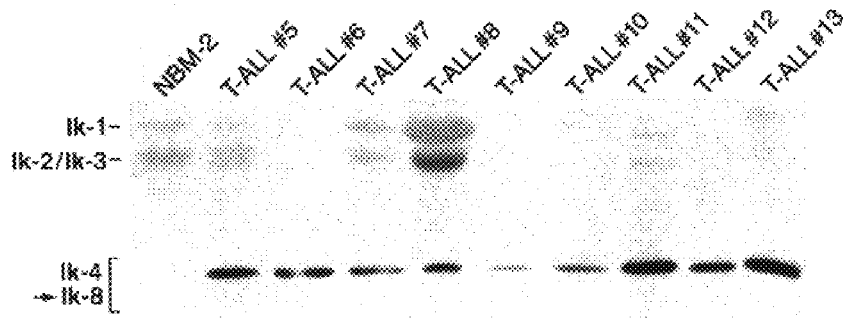
Figure 1G:
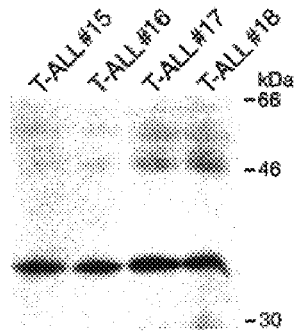

The instant invention relates to the discovery that expression of mutant and/or dominant-negative isoforms of Ikaros correlates with human disease, such as cancer and hematologic disorders, including lymphoid malignancies such as infant stem cell leukemia and T-ALL in children. Accordingly, determining the presence and/or relative amounts of the mutant and dominant-negative isoforms in a sample provides a diagnostic assay for the detection of disease, including cancer, as well as the detection of the presence of abnormal hematologic cells, particularly malignant lymphoid cells, and the like.

Ikaros, a zinc-finger DNA-binding protein, is a critical transcriptional regulator. Regulaton of the Ikaros gene expression during lymphocyte development is in part, mediated by alternative pre-mRNA splicing. Specific Ik-isoforms Ik-1 to Ik-8 have been identified. These isoforms differ in their amino-terminal zinc finger composition and in their DNA binding and transcriptional activation properties.

Only three of the known 8 isoforms (Ik-1, Ik-2, and Ik-3) contain the 3 to 4 N-terminal zinc fingers needed to bind with high affinity to the Ikaros DNA-binding sequence, GGGAAT [SEQ ID NO: 1]. These DNA binding isoforms can localize to the nucleus for binding activity. The remaining isoforms (Ik-4 through Ik-8) contain fewer than the needed 3–4 zinc fingers, and localize to the cytoplasm of the cell.

C-terminal zinc fingers coordinate the formation of homo- and heterodimeric Ik complexes. The formation of homo- and heterodimers among the DNA binding isoforms, Ik-1, 2, and 3, increases their affinity for DNA, whereas heterodimers between the DNA binding isoforms and non-DNA binding isoforms, Ik-4 through 8, are unable to bind DNA.

The abundance of the dominant-negative isoforms (Ik-4 through 8) is correlated herein with hemotologic malignancy, for example, with lymphoid malignancy such as lymphoma and leukemia. The presence of these isoforms in the cytoplasm of lymphoid cells and the absence of the wild type DNA binding isoforms Ik-1, 2, and 3, appears to stabilize the cells against normal programmed cell death, or apoptosis. Furthermore, the presence of mutant isoforms is also correlated herein with hematologic malignancy.

Definitions

All scientific and technical terms used in this application have meanings commonly used in the art unless otherwise specified. As used in this application, the following words or phrases have the meanings specified.

As used herein, "mutation" means alterations in DNA, RNA, or polypeptides relative to the corresponding wild-type DNA, RNA, or polypeptides.

As used herein, "Ikaros isoforms" means alternative splice variants of the Ikaros gene resulting in Ikaros mRNA, cDNA, and protein having variable size and sequence.

As used herein, "mutant Ikaros isoforms" includes both DNA binding Ikaros isoforms (Ikaros 1–3) and non-DNA binding Ikaros isoforms (Ik 4–8) that have either an insertion at exon 2 or a deletion at the splice junction of exon 6–7.

As used herein, "dysfunctional" or "dominant negative" Ikaros isoforms means wild-type non-DNA binding Ikaros isoforms and mutant Ikaros isoforms that interfere with binding DNA at an Ikaros binding site and/or interfere with localization of Ikaros to the nucleus.

As used herein, "DNA binding Ikaros isoforms" include those isoforms having the three or more N-terminal fingers required for high affinity binding to an Ikaros DNA binding site, including Ik-1, Ik-2, and Ik-3.

As used herein, "non-DNA binding Ikaros isoforms" includes those isoforms lacking the one or more of the three N-terminal zinc fingers required for high affinity binding to an Ikaros DNA binding site, including Ik-4, -5, -6, -7, and -8.

As used herein, "treatment" means the prevention of disease induction or progression, and/or the lessening of disease symptoms, including, for example, the reduction of cancer or diseasedt cell numbers.

As used herein, "lymphoid abnormality" or "lymphoid disease" means a disease involving T-cells or B-cells, and includes malignancies or leukemias such as stem cell leukemia, T-cell or B-cell ALL, and secondary leukemia.

Compositions and Methods of the Invention

A. Nucleic Acid Sequences Encoding Mutant Ikaros Polypeptides

The present invention provides newly identified and isolated nucleic acid sequences encoding Ikaros isoforms, including of novel genomic Ikaros DNA sequence at the intron-exon splice site between exons 6 and 7. These include 254 base pairs of novel genomic sequence of the 5' end of the intron adjacent exon 6 shown below and also in FIGS. 11A and 11B:

ATTAAATGAAATACAATAACATAAT-
TAAACTAATCTTTGGTTCCCCTATTTATGTATTCATTTAT

CCAACAAAATCTCCTTAAGTGCT-
TATAATGGGTAGGTCCTGGCTCGGTGTC-
CCCTAGACAGACGC

ATGGGCCTTCCCCCAGCCCGTCAGTATG-
GTGCAGGTGTGATGTGTCCGCAGGTGTGTGTGTATGT

GTGCAGGTGTGGGGTCCGCAGGCGT-
GCTGGGCCCCCAGGCCGTGTTCCCCTTC-
CCCTCCCCGGTT

GTAGATTTCAGCTGTTGCTGCCAGACCT-
GACCGGTTCCGGAGGTGGCCGCGCCCCACTCACTGTC

GCCTGCTTTCCACAGGGGACAAGGGCCT-
GTCCGACACGCCCTACGACAGCAGCGCCAGCTACGAG

AAGGAGAACGAAATGATGAAGTC-
CCACGTGATGGACCAAGCCATCAA-
CAACGCCATCAACTACCT

Figure 12B:
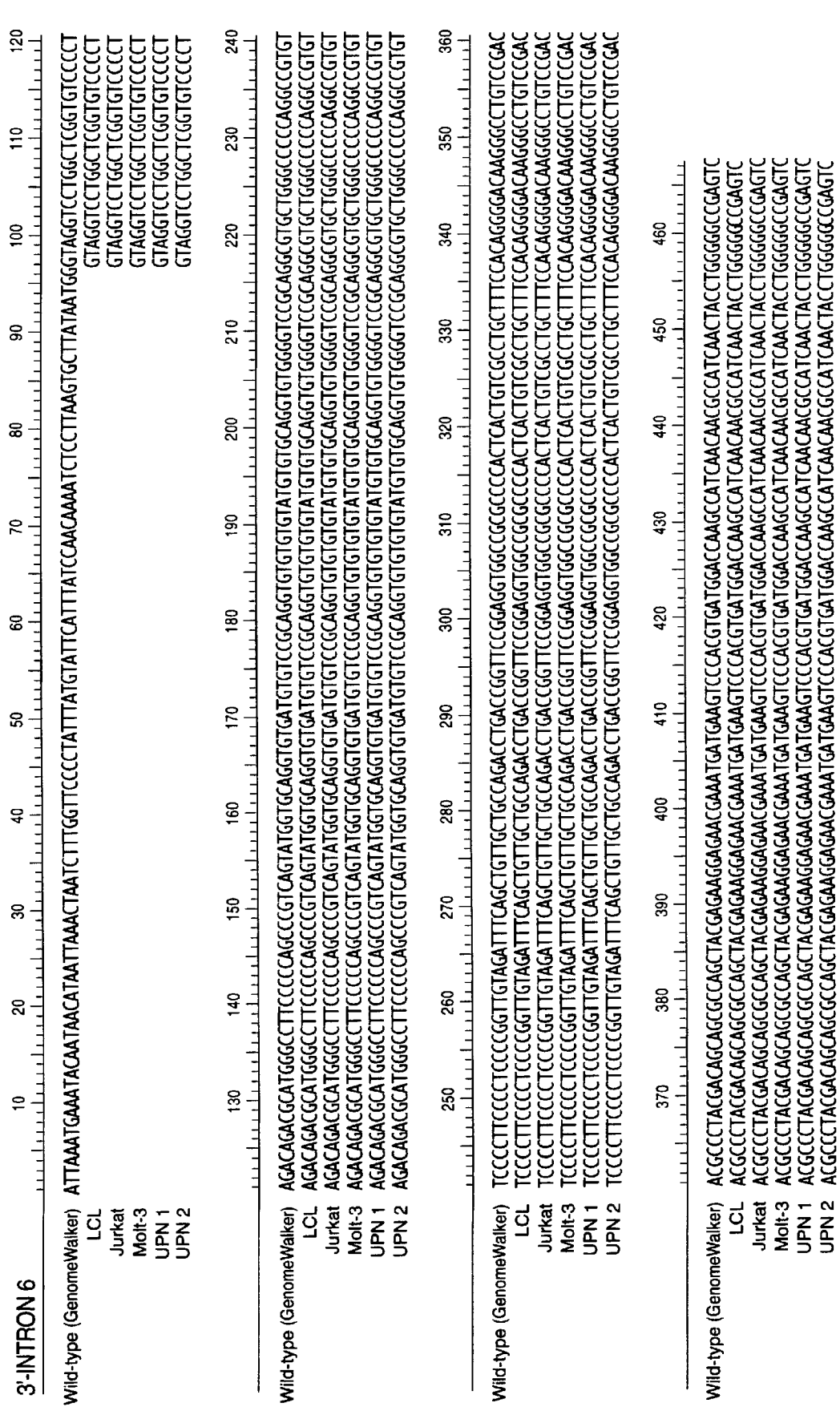

GGGGGCCGAGTC                [SEQ ID NO: 24;]

and 340 base pairs of novel genomic intron sequence adjacent to exon 7 shown below and also in FIGS. 12A and 12B:

TAAGCACAGTGAAATGGCAGAAGACCT-
GTGCAAGATAGGATCAGAGAGATCTCTCGTGCTGGACA

GACTAGCAAGTAACGTCGCCAAACGTAA-
GAGCTCTATGCCTCAGAAATTTCTTGGTAAGAGTTAA

ATGTTTGCTGTCTCTTA A CTATGTGGGTGTTTTAGATG-
CAAGTAGAAATGAGTTGAGG

GTGGAAGAAAGGGAAAAAAATCT-
TATTTTTTCAAAAGGAAAAATTGG-
TAAGCTTAACATTCCTTA

AATATCTTAGAATTTTTTCCAATAAG-
TATCTTAAAAATAACAAACCTCCCATCAGTTTTTCCTAG

ATTTGATTTTGCAGCATCTGGGGCCTGC-
CCTGTGATCTGCCTGTGGAC [SEQ ID NO: 25].

Novel, mutant Ikaros cDNA molecules were also identified. The mutant Ikaros cDNA molecules include those having in-frame deletions at the exon 6–7 splice site, and those having an in-frame insertion at exon 2. Specific mutations are those having a deletion of 30 base pairs encoding a 10 amino acid sequence, KSSMPQKFLG [SEQ ID NO: 13], at exons 6–7 and/or those having a 60 base pair insertion encoding a 20 amino acid sequence, TYGAD-DFRDFHAIIPKSFSR [SEQ ID NO: 11], at exon 2.

B. Anti-mutant Ikaros Antibodies

The present invention further provides anti-mutant Ikaros antibodies that specifically recognize and bind mutant Ikaros polypeptides. Exemplary antibodies include polyclonal, monoclonal, humanized, bispecific, and heteroconjugate antibodies. Preferably, the antibodies of the invention are monoclonal antibodies. Also preferably, the antibody binds a mutant Ikaros polypeptide in the unique region of the mutation (e.g., either the insertion or the unique region generated by the deletion). Most preferably, the antibodies of the invention bind Ikaros polypeptides in a manner that permits detection of a particular mutation. The mutant Ikaros polypeptides, or portions thereof, can be used as antigens to produce antibodies that selectively bind mutant Ikaros isoforms.

Monoclonal antibodies may be prepared using hybridoma methods, such as those described by Kohler and Milstein, 1975, *Nature*, 256:495; by recombinant DNA methods, such as those described in U.S. Pat. No. 4,816,567, or by other methods. The DNA also may be modified, for example, by substituting the coding sequence for human heavy and light chain constant domains in place of the homologous murine sequences [U.S. Pat. No. 4,816,567] or by covalently joining to the immunoglobulin coding sequence all or part of the coding sequence for a non-immunoglobulin polypeptide to create a chimeric antibody. The antibodies may be monovalent antibodies. Digestion of antibodies to produce fragments thereof, particularly, Fab fragments, can be accomplished using routine techniques known in the art.

The antibodies of the present invention can be used in diagnostic assays for mutant Ikaros, for example, detecting the expression or subcellular localization of mutant Ikaros isoforms in a sample of lymphoid cells.

C. Diagnostic Methods

Subcellular Localization of Ikaros

Mutant Ikaros nucleic acid sequences, mutant Ikaros polypeptides, and anti-Ikaros antibodies, including the anti-mutant Ikaros antibodies, provide useful diagnostic tools. For example, diagnostic methods identifying dominant-negative Ikaros isoforms by subcellular localization of Ikaros protein can be used to diagnose lymphoid abnormality. Nuclear compartmentalization of Ikaros protein correlates with the active, normal Ikaros DNA binding isoforms, such as Ik-1, 2 and 3. In contrast, cytoplasmic localization of Ikaros protein correlates with the abundance and presence of the non-DNA binding, dominant-negative isoforms such as Ik4–Ik8, and with disease such as cancer.

Diffuse, non-punctate nuclear localization, diffuse nuclear and/or cytoplasmic localization, and/or cytoplasmic localization of Ikaros protein correlates with lcancer and with ymphoid disease, and in particular, with human hemotologic malignancy. Normal cells demonstrate punctate nuclear localization of Ikaros. This difference in subcellular localization of the Ikaros isoforms can thus be used to diagnose cancer and/or lymphhoid disease.

Methods known for analysis of protein localization may be employed to determine the cellular localization of Ikaros in a patient sample. Immuno-assay employing immunofluorescence staining for the detection of Ikaros is preferred.

Methods known for analysis of protein localization may be employed to determine the cellular localization of Ikaros in a patient sample. Immuno-assay employing immunofluorescence staining for the detection of Ikaros is preferred.

Immunoassay of Ikaros Expression

Specific Ikaros isoforms can be identified, for example, by Western blot analysis, and can also be used to diagnose cancer and lymphoid cell abnormalities. An abundance of dominant-negative isoforms, for example, of one or more of Ik 4–8, correlates with hemotologic cell abnormality. In general a ratio of non-DNA-binding isoforms to DNA-binding isoforms greater than 1 is indicative of lymphoid disease.

The identification of dominant negative Ikaros isoforms by Western blot analysis can also be achieved through determination of the relative sizes of the Ikaros isoforms present in the sample. The dominant negative isoforms, Ik-4–8, have an apparent molecular weight less than that of Ik-2 or Ik3, which is about 47 kDa. Thus, analysis of Ikaros protein in a Western blot analysis using a polyclonal antibody that recognizes all eight wild-type or mutant Ikaros isoforms can be used to determine the relative ratio of dominant negative isoforms (mw less than about 47 kDa) to the DNA-binding isoforms (mw about 47 kDa).

Specific antibodies that discriminate between the DNA-binding and non-DNA-binding isoforms can also be used. For example, reactivity with antibodies directed to an epitope lacking in Ik 4–8 can be used to screen for DNA-binding isoforms.

Nucleic Acid Analysis

Analysis of mutant Ikaros nucleic acid sequences can also be used in diagnostic methods to identify the presence of mutant Ikaros protein, cDNA, RNA, or gene encoding the mutant protein. Because mutant forms of Ikaros are correlated with disease, such as cancer and hemotologic cell abnormality, including human hematologic malignancy the presence of such mutant protein, cDNA, RNA, or genes is diagnostic. Direct sequencing, binding, or hybridization assays including PCR, RT-PCR, Northern blot, Southern blot, and RNAse protection can be used. For example, PCR amplification or RT-PCR amplification of a region of a known Ikaros nucleic acid mutation, such as exon 2 or exons 6–7, are used. The presence of a 21 amino acid insert at exon 2 correlates with hemotologic cell abnormality.

In another embodiment, reverse transcription reactions coupled with PCR amplification of the region at exons 6–7 known to identify the 10 amino acid deletion (30 nucleic acid deletion) can be used to assay for the presence of an Ikaros deletion mutation with hemotologic cell abnormality.

Similarly, reverse transcription reactions coupled with PCR amplification can be used to identify non-mutant non-DNA binding Ikaros isoform, Ik 4–8. The presence of non-mutant non-DNA binding Ikaros isoform, Ik 4–8, correlates with hemotologic cell abnormality, cancer, and particularly lymphoid disease.

Any of these diagnostic methods can be used to detect disease, monitor disease progression and/or regression, and to evaluate the effects of treatments.

D. Treatment Methods
Ikaros Replacement Therapy

An absence or lack of DNA-binding Ikaros isoforms is correlated with lymphoid disease. Therapeutic replacement of DNA binding Ikaros isoforms, Ik 1–3, preferably Ik-1 or Ik-2, is thus desirable. Such replacement can be accomplished by known methods, including administration of DNA-binding forms of IK protein directly; and/or by administration of nucleic acids encoding these proteins for in vivo production.

The invention may be better understood with references to the following, non-limiting examples.

EXAMPLE 1

Characterization of Ikaros Expression in Children with ALL

A. Patients and Cell Lines

The patient population included 64 children (<21 years of age) with newly diagnosed ALL who were enrolled on Children's Cancer Group (CCG) protocols CCG-1882 and CCG-1961 (for ALL patients of age 1–9 years with WBC $\geq 50,000/\mu l$ or age $\geq 10$ years), CCG 1901 (for ALL patients with lymphomatous features, including T-ALL), or CCG-107, CCG-1883 and CCG-1953 (for infants with ALL). Fifteen patients had T-lineage ALL and 49 patients had B-lineage ALL. Except for 8 patients with B-lineage ALL, all other patients (87.5%) had high risk ALL according to the NCI risk classification (Smith et al., 1996, *J. Clin. Oncol.*, 14:18–24). Five patients in first bone marrow relapse also were studied.

Each protocol was approved by the National Cancer Institute as well as the Institutional Review Boards of the participating CCG-affiliated institutions. Informed consent was obtained from parents, patients, or both, as deemed appropriate, for both treatment and laboratory studies, according to Department of Health and Human Services guidelines.

Diagnosis of ALL was based on morphological, biochemical, and immunological features of the leukemic cells, including lymphoblast morphology as determined by Wright-Giemsa staining, positive nuclear staining for terminal deoxynucleotidyl transferase, negative staining for myeloperoxidase, and reactivity with monoclonal antibodies to lymphoid differentiation antigens, as described previously (Uckun et al., 1996, *Leuk. Lymphoma*, 24:57–70; Uckun et al., 1997, *Blood*, 90:28–35; and Uckun et al., 1997, *J. Clin. Oncol.*, 15:2214–2221). All T-lineage ALL were classified as T-lineage ALL because $\geq 30\%$ of the isolated leukemic cells were positive for the pan-T cell marker CD7 and <30% were positive for the pan-B cell marker CD19. Similarly, all B-lineage ALL patients were classified as B-lineage ALL because $\geq 30\%$ of their leukemic cells were positive for CD19 and <30% were positive for CD7. Surplus cells from diagnostic bone marrow specimens were used for molecular genetic studies. The presenting clinical features of the 64 newly diagnosed patients are shown in Table 1. Among the 15 newly diagnosed T-lineage ALL patients, all 15 had high risk ALL according to the NCI risk classification (Smith et al., 1996, *J. Clin. Oncol.*, 14:18–24), 9 (60%) were male, 14 (97%) had high white blood cell counts, 12 (80%) had hepatosplenomegaly, and 11 (73%) had a mediastinal mass (Table 1). Among the 49 newly diagnosed B-lineage patients, 41 (30 infants and 11 children) (84%) had high risk ALL, 28 (57%) were male, 27 (55%) had high white blood cell counts, and 34 (69%) had hepatosplenomegaly.

Normal bone marrow specimens were obtained from two children who were bone marrow donors in the context of sibling bone marrow transplantation. Normal thymuses were obtained from 5 children undergoing thoracic surgery for a cardiac defect. One fetal thymus was obtained from a prostaglandin-induced human abortus of 21 weeks gestational age. These tissues were used according to the guidelines of the Hughes Institute Committee on the Use of Human Subjects. In addition, the human T-ALL cell lines MOLT-3 and JK-E6-1 (ATCC TIB-152), as well as the B-lineage ALL cell lines LC1;19 (E2A-PBX1$^+$), KM-3, HPB-NULL, NALM-6, ALL-1 (BCR-ABL$^+$), and RS4;11 (MLL-AF4$^+$) were also included in the analyses. Also included were the fetal liver derived immature lymphocyte precursor cell lines FL8.2$^+$ (a CD2$^+$, CD19$^+$, CD10$^+$, CD34$^+$ pro-B/T cell line with germline IgH and TCR$\alpha/\beta$ genes coexpressing the B-lineage surface antigen CD19 as well as the T-lineage surface antigen CD2) and FL8.2$^-$ (a CD2$^-$ CD19$^+$CD10$^+$CD34$^+$C$\mu^-$sIg$^-$ pro-B cell line with germline IgH genes). These normal lymphocyte precursor cell lines were established and characterized as reported in Uckun et al., 1989, *Blood*, 73: 1000–1015; and Uckun et al., 1991, *Proc. Natl. Acad. Sci. USA*, 88:3589–3593.

TABLE 1

Patient Characteristics

| Patient Subgroup | Characteristic | Value |
|---|---|---|
| T-Lineage All (N = 15)* | Categorical Variables | No. of Patients (%) |
| | High risk | 15 (100) |
| | Male sex | 9 (60) |
| | WBC > 50 × 10$^9$/L | 14 (97) |
| | Hepatosplenomegaly | 12 (80) |
| | Mediastinal mass | 11 (73) |
| | Continuous variables | mean ± SE (Range) |
| | Age - yr | 8.1 ± 1.0 (1.8–19.0) |
| | WBC - ×10$^9$/L | 389 ± 65 (7–819) |
| B-Lineage All (N = 49)† | Categorical Variables | No. Of Patients (%) |
| | High risk†† | 41 (84) |
| | Male sex | 28 (57) |
| | WBC > 50 × 10$^9$/L | 27 (55) |
| | Hepatosplenomegaly | 34 (69) |
| | Continuous variables | mean ± SE (Range) |
| | Age - yr | 3.4 ± 0.7 (0.1–18.8) |
| | WBC - ×10$^9$/L | 203 ± 40 (3–1,000) |

*In addition to these 15 newly diagnosed patients, 3 patients in first bone marrow relapse were also studied.
†In addition to these 49 newly diagnosed patients, 2 patients in first bone marrow relapse were also studied.
††The high risk B-lineage All subgroup included 30 infants (<12 months of age) with all and 11 children with high risk ALL.

B. Cytogenetic Analysis

Cytogenetic analysis of leukemic cells was performed by local institutions prior to initiation of therapy. Banded chromosomes were prepared from unstimulated peripheral blood or direct and 24-hour cultured preparations of fresh bone marrow, as described by Heerema et.al., 1985, *Cancer, Genet, Cytogenet.*, 17:165–179). Chromosome abnormalities were designated using the 1995 International System for Human Cytogenetics Nomenclature (Mitelman, 1995, IN: *ISCN: An International System for Human Cytogenetic Nomenclature*, (Karger)). Abnormal clones were defined as 2 or more metaphase cells with identical structural chromosomal abnormalities or extra chromosomes, or 3 or more metaphase cells with identical missing chromosomes.

C. Analysis of Ikaros Protein Expression by Western Blot

Ikaros expression was studied in 8 different ALL cell lines, normal tissues, and primary leukemic cells from 59 children with ALL by Western blot analysis of proteins contained in whole cell lysates using polyclonal anti-Ikaros antibody that recognizes all eight Ikaros isoforms.

Methods

Whole cell lysates were prepared using a 1% Nonidet-P40 lysis buffer, as described by Uckun et al., 1996, *Science*, 273:1096–1100; and Sun et al., 1999, *Proc. Natl. Acad. Sci. USA*, 96(2):680–685. Western blot analysis of whole cell lysates for Ikaros expression was performed using a polyclonal anti-Ikaros antibody, described in Sun et al., 1996, *EMBO J*, 15:5358–5369, reactive with all eight Ikaros isoforms as described by Uckun et al., 1996, *Science*, 273:1096–1100; and Sun et al., 1999, *Proc. Natl. Acad. Sci. USA*, 96(2):680–685. In brief, 30 µg samples of whole cell lysates were loaded on a 12% SDS-PAGE gel and the size-fractionated proteins were transferred onto a PVDF membrane (Millipore). The membrane was blocked in 5% milk for at least one hour at room temperature and then incubated with a polyclonal anti-Ikaros antibody (1:1000 dilution) (Sun et al., 1996, *EMBO J*., 15:5358–5369) in PBS with 5% milk over night at 4° C. The membrane was washed three times with PBST (150 mM NaCl, 16 mM $Na_2HPO_4$, 4 mM $NaH_2PO_4$, 0.1% Tween, pH 7.3) at room temperature and incubated with a peroxidase-conjugated goat anti-rabbit IgG (1:2000 dilution) (Jackson Lab.) for two hours at room temperature. Immunoreactive proteins were detected by the enhanced chemiluminescence (ECL) system (Amersham), as described by Uckun et al., 1996, *Science*, 273:1096–1100; and Sun et al., 1999, *Proc. Natl. Acad. Sci USA*, 96(2): 680–685.

Results

Results of this study are shown in FIGS. 1A–1G and in Table 2. Normal fetal liver-derived human lymphocyte precursor cell lines $FL8.2^+$ (pro-B/T) and $FL8.2^-$ (pro-B) (FIG. 1A) as well as normal bone marrow cells and thymocytes (FIGS. 1B, C, D and G, Table 2) expressed a 57 kDa immunoreactive protein corresponding in size to Ik-1, and a 47 kDa immunoreactive protein corresponding to either Ik-2 or Ik-3. In contrast, the T-lineage ALL cell lines MOLT-3 cells and JK-E6-1 (FIG. 1E, Table 2 legend), B-lineage ALL cell lines LC1;19, KM-3, HPB-NULL, NALM-6, ALL-1, and RS4;11 (FIG. 1B), and primary leukemic cells from 16 of 17 (94%) T-lineage ALL patients (FIGS. 1E–1G, Table 2) and 42 of 42 (100%) B-lineage ALL patients (Table 2, FIG. 1C and G) primarily expressed a smaller immunoreactive protein band of approximately 37–40 kDa, corresponding in size and electrophoretic mobility to one or more of the small non-DNA binding Ikaros isoforms Ik-4, Ik-5, Ik-6, Ik-7, and/or Ik-8.

In summary, normal cells expressed the large (about 47 KD or greater), DNA-binding Ikaros isoforms, Ik 1–3, whereas leukemic cells of T and B cell lineage expressed an abundance of the smaller (<47 KD), non-DNA-binding isoforms (Ik 4–8).

Abnormal Subcellular Compartmentalization

The subcellular compartmentalization of Ikaros proteins in normal and fetal tissues was compared to that in primary leukemic cells from 49 children with ALL (11 T-lineage and 38 B-lineage ALL patients), 2 ALL cell lines, and 2 normal fetal liver lymphocyte precursor cell lines ($FL8.2^+$ and $FL8.2^-$) by confocal laser scanning microscopy.

Methods

The subcellular localization of Ikaros protein(s) was examined by immunofluorescence and confocal laser scanning microscopy, as described by Uckun et al., 1996, *Science*, 273:1096–1100; and Sun et al., 1999, *Proc. Natl. Acad Sci. USA*, 96(2):680–685. Cells ($200\times10^3$) were attached to poly-L-lysine-coated glass coverslips by a 30 minutes incubation at room temperature, washed twice with PBS, and fixed in ice cold (−20° C.) methanol for 15 minutes. In order to permeabilize the cells and block the non-specific antibody binding sites, cells were treated with 0.1% Triton X-100 and 10% goat serum in PBS for 30 minutes.

To detect the Ikaros protein, cells were incubated with an affinity-purified polyclonal rabbit anti-Ikaros antibody, described in Sun et al., 1996, *EMBO J*., 15:5358–5369; and Sun et al., 1999, *Proc. Natl. Acad Sci. USA*, 96(2):680–685, (1:300 dilution) for 1 hour at room temperature. Cells were washed with PBS and incubated with a FITC-conjugated goat anti-rabbit IgG (Amersham Corp., Arlington Heights, Ill.) (1:40 final dilution) for 1 hour. Cells were washed with PBS, counterstained with the DNA-specific nuclear dye toto-3 (Molecular Probes, Inc.; 1:1000 dilution) for 10 minutes at room temperature, and washed again with PBS. The coverslips were inverted, mounted onto slides in Vectashield (Vector Labs, Burlinghame, Calif.) to prevent photobleaching and sealed with nail varnish as described by Sun et al., 1999, *Proc. Natl. Acad. Sci. USA*, 96(2):680–685. Slides were examined using a Bio-Rad MRC 1024 Laser Scanning Confocal Microscope mounted on an Nikon Eclipse E-800 upright microscope equipped for epifluorescence with high numerical aperture objectives as in Uckun et al., 1996, *Science*, 273:1096–1100; and Sun et al., 1999, *Proc. Natl. Acad. Sci. USA*, 96(2):680–685. Optical sections were obtained and turned into stereomicrographs using Lasersharp software (Bio-Rad, Hercules, Calif.). Representative digital images were processed using Adobe Photoshop software (Adobe Systems, Mountain View Calif.). Images were printed with a Fuji Pictography thermal transfer printer (Fuji Photo, Elmsford, N.Y.).

Results

Figure 2A:
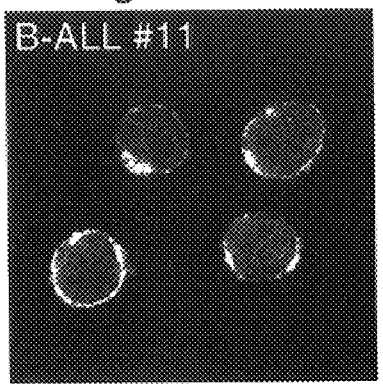
FIGS. 2A–2S are confocal images of leukemic cells showing expression and subcellular localization of Ikaros.
Figure 2B:
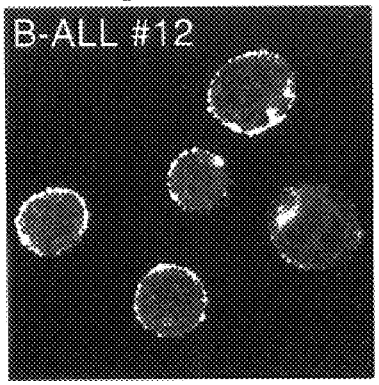
Figure 2C:
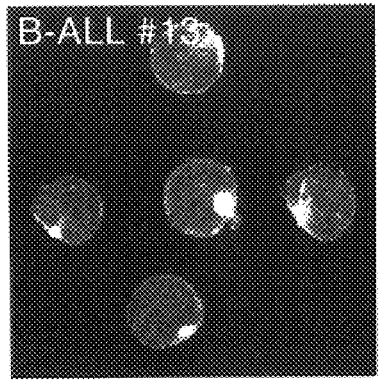
Figure 2L:
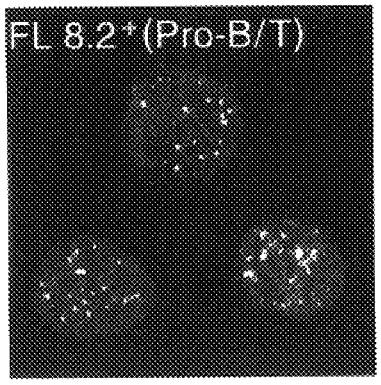
FIGS. 2L and 2M show normal fetal liver-derived lymphocyte precursor cell lines FL8.2$^+$ (Pro-B/T) and FL8.2$^-$ (Pro-B), respectively.
Figure 2M:
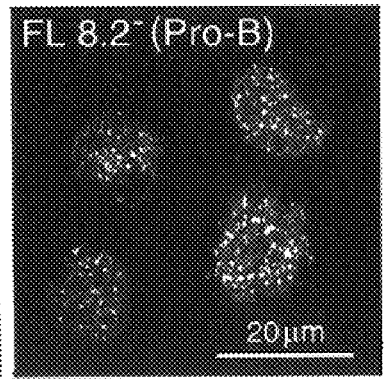
Figures 2D, 2E, 2F, 2G, 2H, 2I, 2J, 2K:
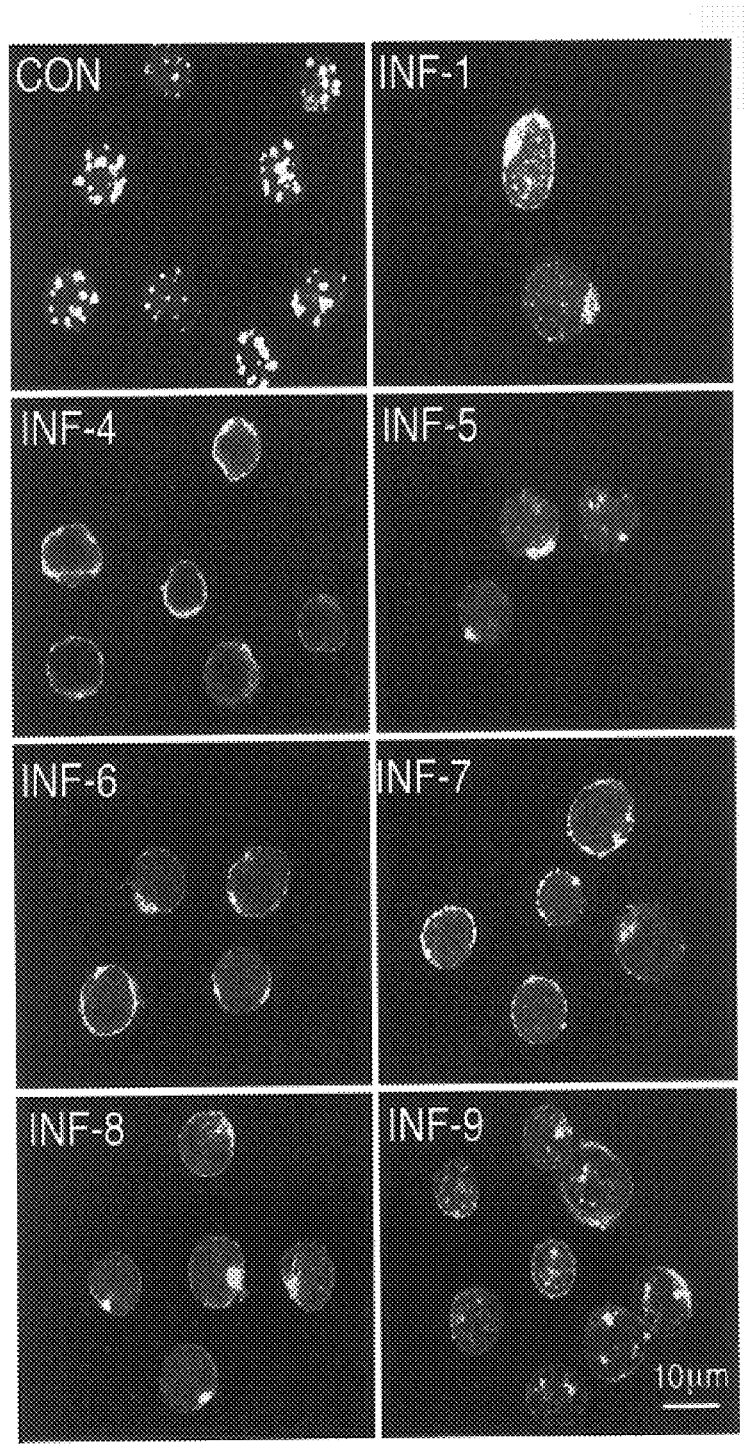
Figure 2N:
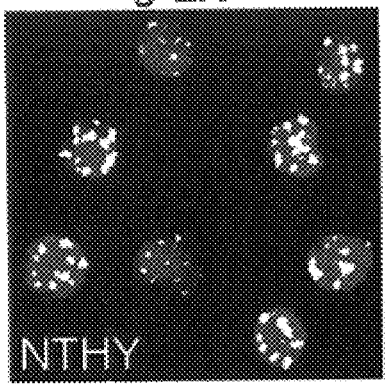
FIG. 2N shows normal thymocytes.
Figure 2O:
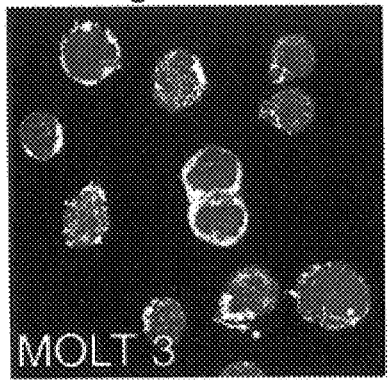
FIGS. 2O and 2P show leukemic T-cells MOLT-3 cells and JK-E6-1 cells, respectively.
Figure 2P:
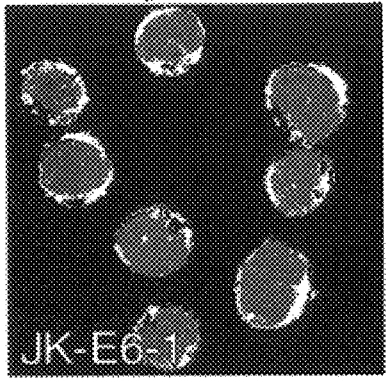

The nuclei (but not the cytoplasm) of FL8.2+ and FL8.2− cell lines (FIGS. 2L & M), fetal thymocytes, normal thymocytes (FIG. 2O) and normal bone marrow mononuclear cells (Table 2) were stained brightly by the anti-Ikaros antibody with discrete foci of high level expression, as evidenced by a distinct punctate green fluorescent staining pattern in toto-3 labeled blue nuclei.

Figure 2Q:
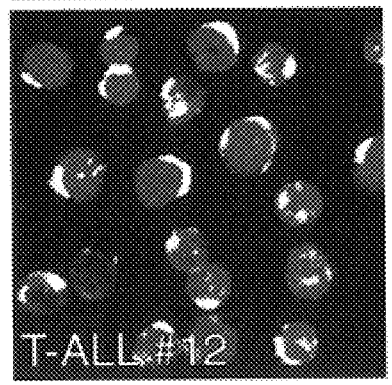
Figure 2R:
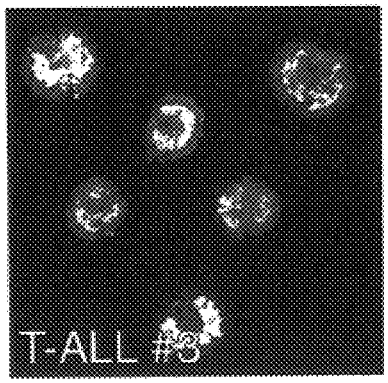
Figure 2S:
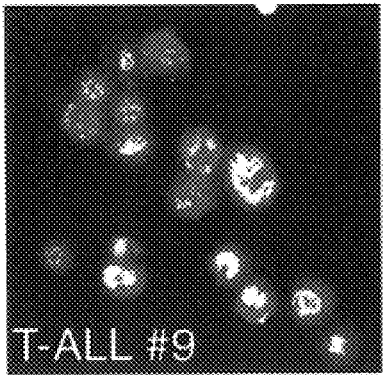

In contrast, Ikaros proteins were expressed predominantly in the cytoplasm of leukemic cells from 7 of 11 children (64%) with T-lineage ALL (FIGS. 2Q–R), 20 of 38 children (53%) with B-lineage ALL (FIGS. 2A–K) as well as the ALL cell lines JK-E6-1 (FIG. 2–O) and MOLT-3 (FIG. 2O), as evidenced by a bright green fluorescent rim surrounding the toto-3 labeled blue nuclei. In leukemic cells from 4 of 11 (36%) T-lineage ALL patients and 18 of 38 (47%) B-lineage ALL patients, an abnormal diffuse, "patchy" nuclear staining with or without cytoplasmic staining was found (Table 2).

In summary, the data show nuclear localization of Ikaros protein in normal cells, but diffuse and/or cytoplasmic staining of Ikaros protein in leukemic cells.

E. Loss of Ikaros-Specific DNA Binding Activity in Leukemic T-Cells

The ability of nuclear extract proteins from normal thymocytes and leukemic T-cells to exhibit Ikaros-specific high affinity DNA binding activity was assessed in gel mobility shift assays (EMSA) using the Ik-BS1 oligonucleotide probe that contains a single high affinity Ikaros binding site. The data are shown in FIG. 3.

Methods

Nuclear extracts were prepared by the method of Dignam et. al.,1983, *Nucleic Acid Res.*, 11:1475–1489. The Ik-BS1 oligonucleotide is shown here with the Ikaros binding site in bold.

5'TCAGCTTTTGGGAATACCCTGTCA3'  [SEQ ID NO: 2]

The probe was end-labeled with $^{32}$P using T4 polynucleotide kinase and $\gamma^{32}$P-ATP (3,000 Ci/mmol) and purified using a Nuctrap probe purification column (Stratagene). Prior to addition of labeled probe, the nuclear extracts (3 µg) were preincubated for 10 minutes at room temperature in a 20 µl reaction mixture containing 10 mM HEPES, pH 7.9, 50 mM KCl, 2 mM DTT, 0.2 mM EDTA, 10% glycerol and 2 ng poly dI-dC/dI-dC. Labeled probe (1 ng; 1×10$^5$ cpm/ng) was added and the mixture was incubated for an additional 20 minutes at room temperature. Reactions were terminated by the addition of gel loading buffer. For competition reactions, 60-fold excess unlabeled specific or nonspecific probes were added prior to the preincubation. The Ik-BS1 oligonucleotide was used as the specific competitor and the Ik-BS1M oligonucleotide. This oligonucleotide contains a 2-base pair mutation at the Ikaros binding site.

5'TCAGCTTTTGGGggTACCCTGTCA3  [SEQ ID NO: 3]

Electrophoresis was carried out using 7% acrylamide:bisacrylamide (37.5:1)(pH 8.3) Tris-Glycine-EDTA gel containing 4% glycerol. Gels were pre-run at 150 V for 2 hours at 4° C. Reaction mixtures (15 µl) were loaded and electrophoresed for an additional 4 hours. Following electrophoresis, gels were dried and subjected to autoradiography on film.

Results

The results of the mobility shift assay are shown in FIGS. 3A and 3B. Nuclear proteins from normal thymocytes (NTHY) revealed mobility shifts consistent with significant Ikaros-specific DNA-binding activity (FIG. 3A): Three major shifted bands, which correspond to protein-DNA complexes containing Ikaros monomers, dimers, and higher order multimeric complexes, were detected. This triplet binding pattern was specific, since 60-fold excess of the unlabeled wildtype Ik-BS1 oligonucleotide was able to inhibit the mobility shift, but not the mutant Ik-BSM oligonucleotide probe with a two base pair mutation at the Ikaros binding site (lanes 3 vs. 4, respectively).

In contrast to extracts from normal thymocytes, nuclear extracts from MOLT-3 cell line or leukemic T-cells of T-ALL patients revealed no detectable mobility shifts of the Ik-BS1 probe (FIG. 3B).

These results provide unprecedented evidence that nuclear proteins from leukemic cells lack Ikaros-specific high affinity DNA binding activity. These results are consistent with the confocal images of leukemic cells showing Ikaros expression in the cytoplasm, but not in the nucleus, of leukemic cells. Additionally, the absence of Ikaros activity in leukemic cells with an abnormal patchy-diffuse (instead of punctate or speckled) nuclear Ikaros staining pattern indicates altered DNA binding properties of Ikaros-containing complexes in some of the ALL patients.

TABLE 2

Ikaros Expression Profile of Leukemic Cells from Children with Acute Lymphoblastic Leukemia

| Predominant Pattern of Ikaros Expression | No. of cases (%) | | |
|---|---|---|---|
| | T-lineage | B-Lineage | Normal Thymus/Bone Marrow |
| Confocal Imaging of Location | | | |
| Cytoplasmic | 7/11 (64) | 20/38 (53) | 0/7 (0) |
| Nuclear, diffuse | 5/11 (36) | 18/38 (47) | 0/7 (0) |
| Nuclear, focal (normal) | 0/11 (0) | 0/38 (0) | 7/7 (100) |
| Western Blot Analysis | | | |
| Small isoforms (Ik4→Ik8) | 16/17 (94) | 42/42 (100) | 0/9 (0) |
| Large isoforms (Ik1→Ik3) | 1/17 (6) | 0/42 (0) | 9/9 (100) |
| PCR Cloning & Sequencing | | | |
| Wild-type DNA Binding Isoforms | 0/10 (0) | 0/11 (0) | 2/2 (100)** |
| Mutant DNA Binding Isoforms and/or Dominant-Negative Isoforms smaller than Ik-2 | 10/10 (100) | 11/11 (100) | 0/2 (0) |
| Ik-2 (ins)† | 1/10 (10) | 0/11 (0) | 0/2 (0) |
| Ik-4 or Ik4 (del)†† | 8/10 (80) | 5/11 (45) | 0/2 (0) |
| Δ KSSMPQKFLG | 6/10 (60) | 9/11 (82) | 0/2 (0) |
| IK-6††† | 0/10 (0) | 1/11 (9) | 0/2 (0) |
| Ik-7 or Ik-7 (del) | 0/10 (0) | 2/11 (18) | 0/2 (0) |
| Ik-8 (del) | 6/10 (60) | 3/11 (27) | 0/2 (0) |

*Because of rounding, the percentages do not always total 100.
**A wild-type Ik-1 was found in 10 of 10 PCR clones from fetal thymocytes and a wild-type Ik-2 was found in 3 of 3 PCR clones from normal bone marrow cells of a healthy child.
†Leukemic cells from T-ALL#14 expressed aberrant Ik-2 isoforms with a 60 bp insertion at the 5' end of exon 3 either alone (5 of 6 PCR clones) or together with a 30 bp deletion at the 3' end of exon 6 (1 of 6 PCR clones). The same aberrant Ik-2 isoform [Ik-2(ins)] was also found in 6 of 10 PCR clones from the T-All cell line MOLT-3. The remaining 4 PCR clones for MOLT-3 were Ik-8.
††An aberrant form of Ik-4 with a 30 bp deletion at the 3' end of exon 6 was found in leukemic cells from 9 children. The same deletion was also found in aberrant Ik-2, Ik-7, or Ik-8 isoforms from 6 additional children.
†††A wild-type Ik-6 was found in 5 of 5 PCR clones from leukemic cells of a standard risk B-lineage ALL patient.

EXAMPLE 2

Molecular Characterization of Ikaros Transcripts in Leukemic Cells

Figure 4:
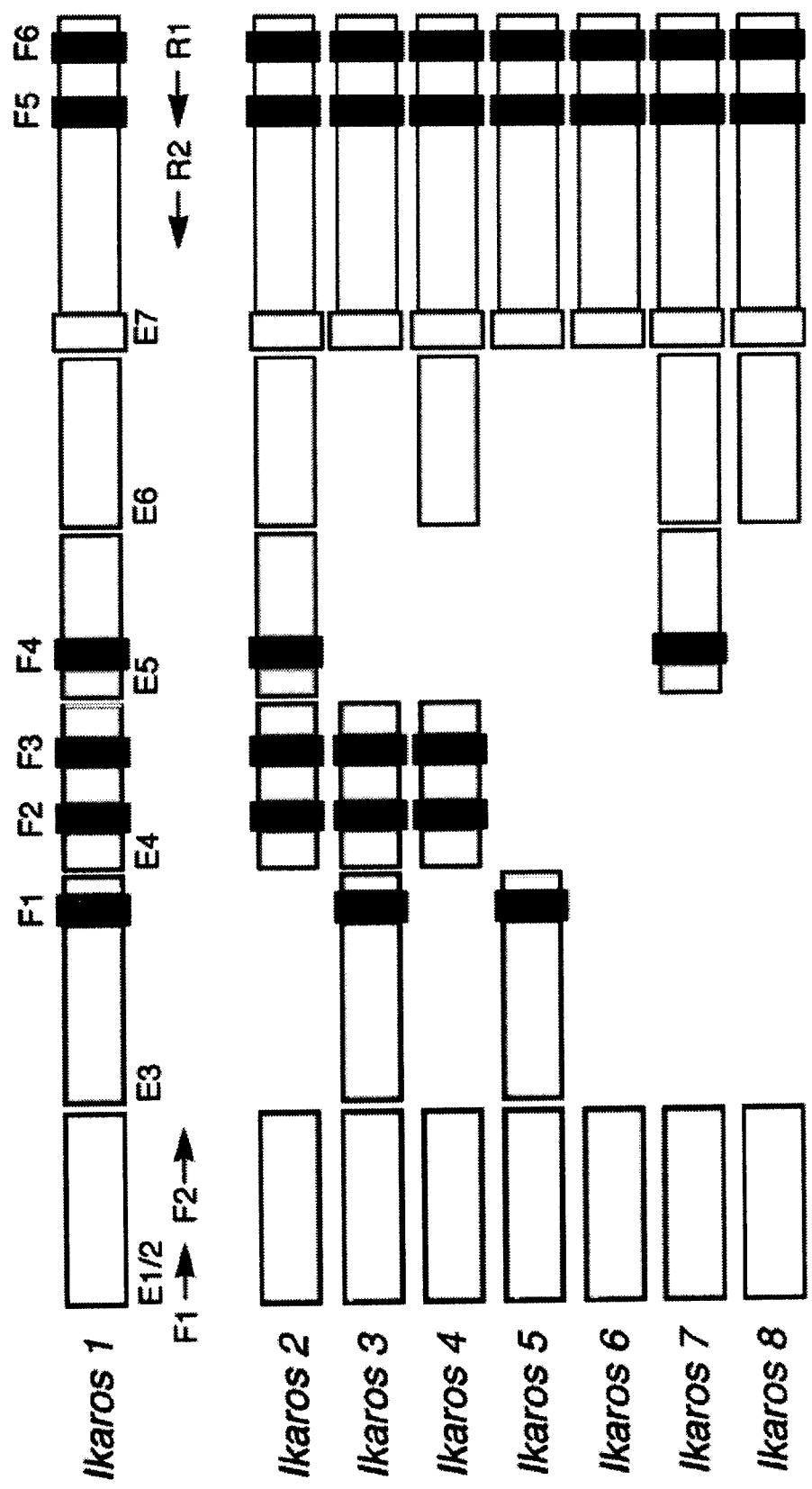
FIG. 4 is a schematic representation of Ikaros isoforms 1–8 with specific composition domains encoded by exons (E) 1–7 and the PCR primers noted.

Nested RT-PCR and nucleotide sequencing were used to examine normal thymocytes, normal bone marrow cells, and leukemic cells from children with ALL for the expression of PCR amplifiable Ikaros transcripts. Purified PCR products were characterized by nucleotide sequencing. FIG. 4 is a schematic diagram showing Ikaros isoforms 1–8, and particularly showing the composition of domains encoded by exons (E) 1–7 as well as the location of PCR primers.

Methods

All RT-PCR assays for Ikaros mRNA expression were performed centrally in the CCG ALL Biology Reference Laboratory, with all due precautions to avoid false positive results, as described in detail by Uckun et al., 1998, *Blood*, 92:810–821. Briefly, total cellular RNA was extracted from cells using the RNeasy™ total RNA isolation kit (Qiagen, Santa Clarita, Calif.), and 20% of the total RNA sample was used for cDNA synthesis with Moloney murine leukemia virus (MMLV) reverse transcriptase (GIBCO-BRL, Gaithersburg, Md.) in the presence of dNTPs. Products were amplified with Amplitaq DNA polymerase (Perkin Elmer Cetus Corp., Norwalk, Conn.) and subjected to 35 cycles in a DNA thermal cycler as described. For enhanced sensitivity, the PCR products were amplified further by nested PCR. Primers for amplification of Ikaros (1k) cDNAs were:

F1: 5'ATGGATGCTGACGAGGGTCAAGAC3' [SEQ ID NO: 4];

and

R1: 5'TTAGCTCATGTGGAAGCGGTGCTC3' [SEQ ID NO: 5].

Primers for nested PCR were:

F2: 5'CTCATCAGGGAAGGAAAGCC3' [SEQ ID NO: 6];

and

R2: 5'GGTGTACATGACGTGATCCAGG3' [SEQ ID NO: 7].

The location of the 5' ends of the primers relative to the start site based on Ik1 cDNA are +1 for F1, +32 for F2, +1570 for R1 and +1444 for R2, respectively. The predicted sizes of the PCR products are 1.5 Kb for Ik1, 1.28 Kb for Ik2 and Ik3, 1.17 Kb for Ik4, 1.1 Kb for Ik5, 0.86 Kb for Ik6, 1.1 Kb for Ik7, and 1.0 Kb for Ik8, respectively.

RNA integrity was confirmed by PCR amplification of the cABL mRNA, which is expressed ubiquitously in human hematopoietic cells, using the primers:

5'-TTCAGCGGCCAGTAGCATCTGACTT-3' [SEQ ID NO: 8];

and

Figure 5A:
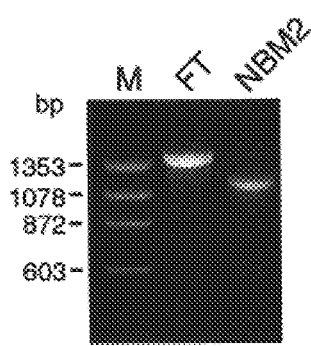
FIGS. 5A–5C are representative ethiduim bromide stained gels showing PCR products amplified from fetal thymocytes (FT), normal bone marrow mononuclear cells (NBM-2), Molt-3 cells, Jurkat cells (JK-E6-1), and primary leukemic cells from patients with T-ALL (T-ALL) and B-ALL (INF).
Figure 5B:
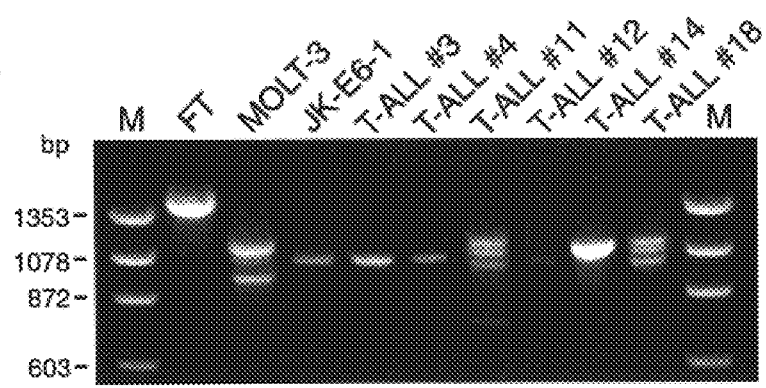
Figure 5C:
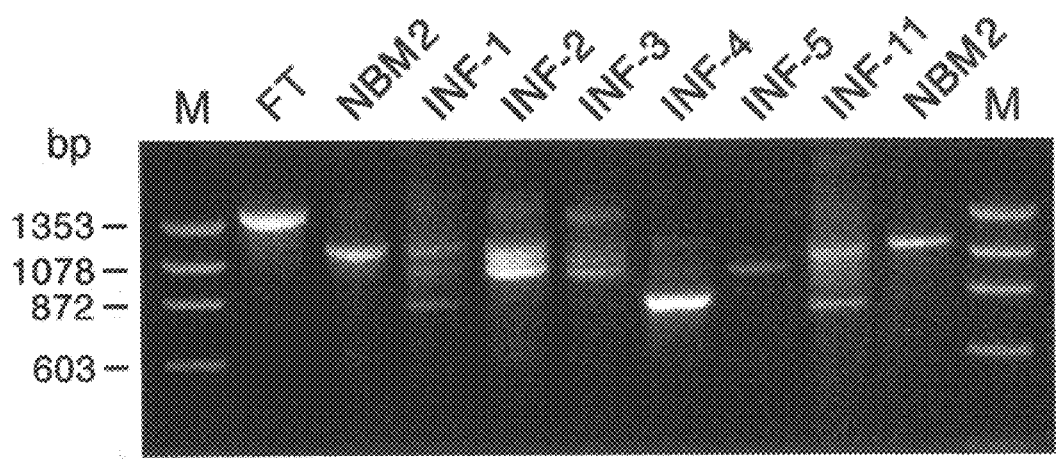

5'-TGTGATTATAGCCTAAGACCCGGAG-3' [SEQ ID NO: 9].

approximately 1.4 Kb was observed in normal fetal thymocytes and 10/10 different PCR clones had the coding sequence of wildtype Ik-1 (FIG. 5A, Table 2). Similarly, a single PCR product of approximately 1.2 Kb was detected in normal bone marrow cells from a healthy child (NBM-2) and 3/3 different PCR clones had the coding sequence of wildtype Ik-2 (FIG. 5A, Table 2). By comparison, the predominant PCR amplification products in leukemic cells from 20 of 21 children with ALL were smaller than Ik-2 (FIGS. 5B & 5C, Table 2).

Figure 6:
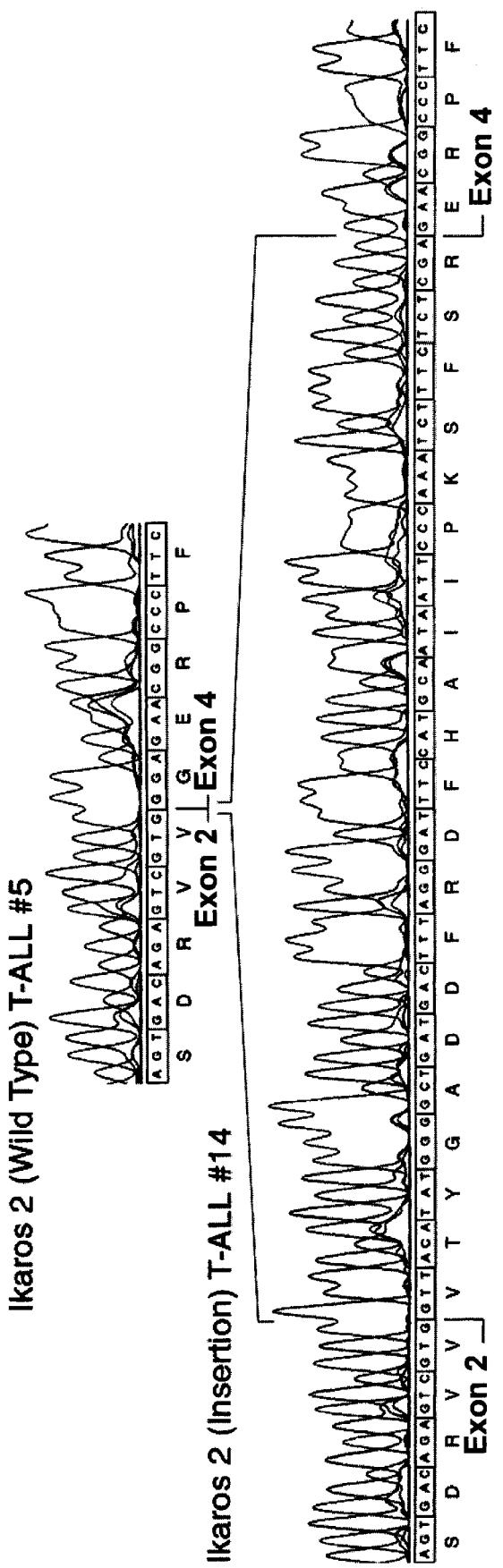
FIG. 6 is a sequence tracing spanning the junction between exon 2 and exon 4 from a control clone (T-ALL#5) having wild-type Ik-2 coding sequence at exons 2–4 and from a T-ALL patient cells (T-ALL#14) showing the IK-2 insertion mutant.
Figure 7:
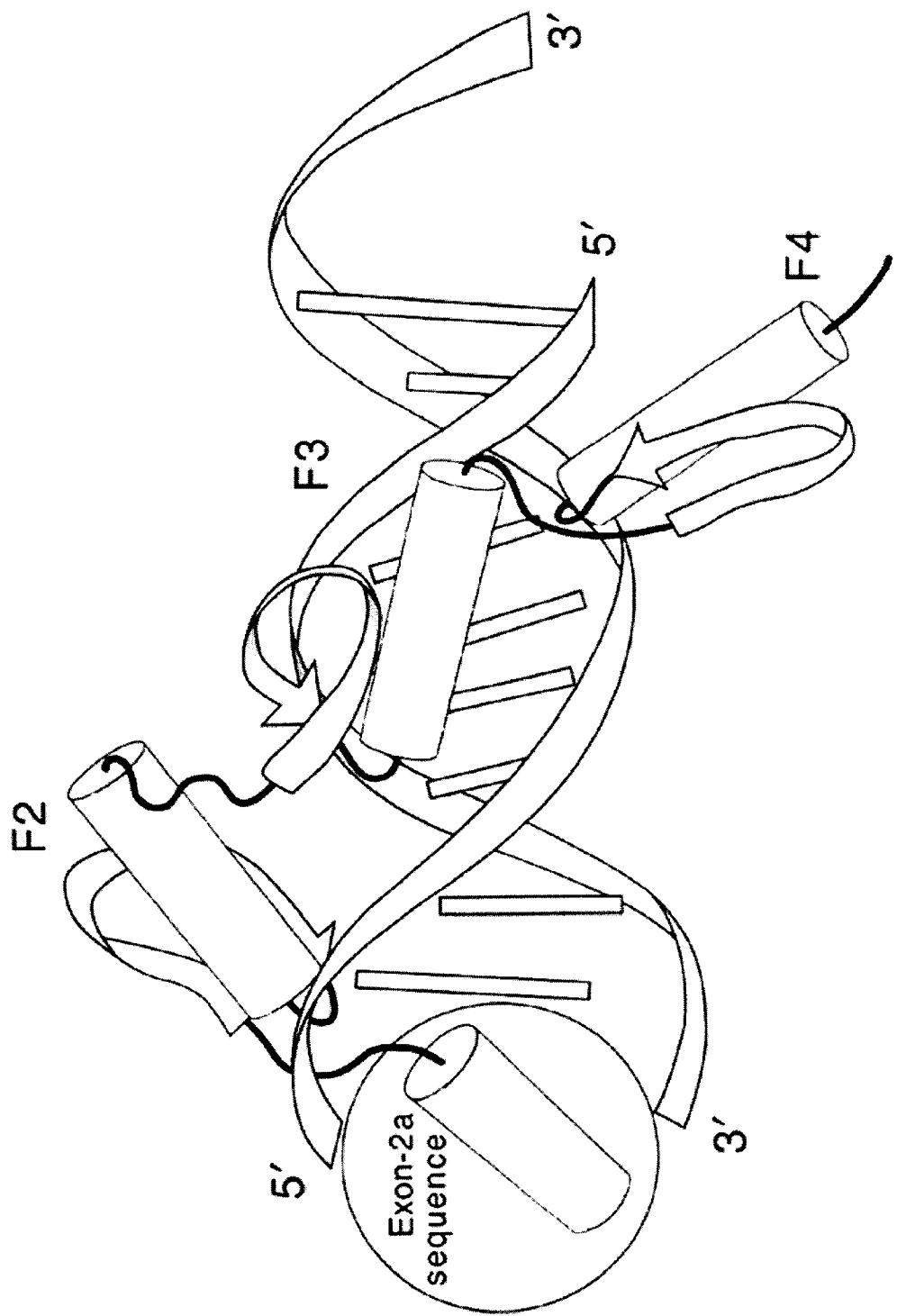
FIG. 7 is a ribbon diagram illustrating the interraction of the first three zinc fingers (F2, F3, and F4) of Ik-2 interact with the major groove of a DNA duplex.

Sequence analysis was successful in all 21 cases. Leukemic cells from one (a T-ALL patient) of the 21 ALL patients, as well as from the T-ALL cell lines, MOLT-3 and JK-E6-1, expressed aberrant Ik-2 isoforms (Ik-2(ins)) having a 20 amino acid insertion (exon 2a) due to a 60-base pair insertion immediately upstream of exon 4 at the exon 2/exon 4 junction (FIG. 6). These cells expressed the insertion mutant either alone, or together with an in-frame 10 amino acid deletion due to a 30-base pair deletion at the 3' end of exon 6 (FIGS. 8A–8C; Table 2).

```
Insert:    GTT ACA TAT GGG GCT GAT GAC TTT AGG GAT TTC CAT GCA ATA
            V   T   Y   G   A   D   D   F   R   D   F   H   A   I ATT CCC AAA TCT TTC TCT CGA                              [SEQ ID NO: 10]
            I   P   K   S   F   S   R                                [SEQ ID NO: 11]

Deletion: T AAG AGC TCT ATG CCT CAG AAA TTT CTT GG                   [SEQ ID NO: 12]
            K   S   S   M   P   Q   K   F   L   G                    [SEQ ID NO: 13]
```

Figure 8B:
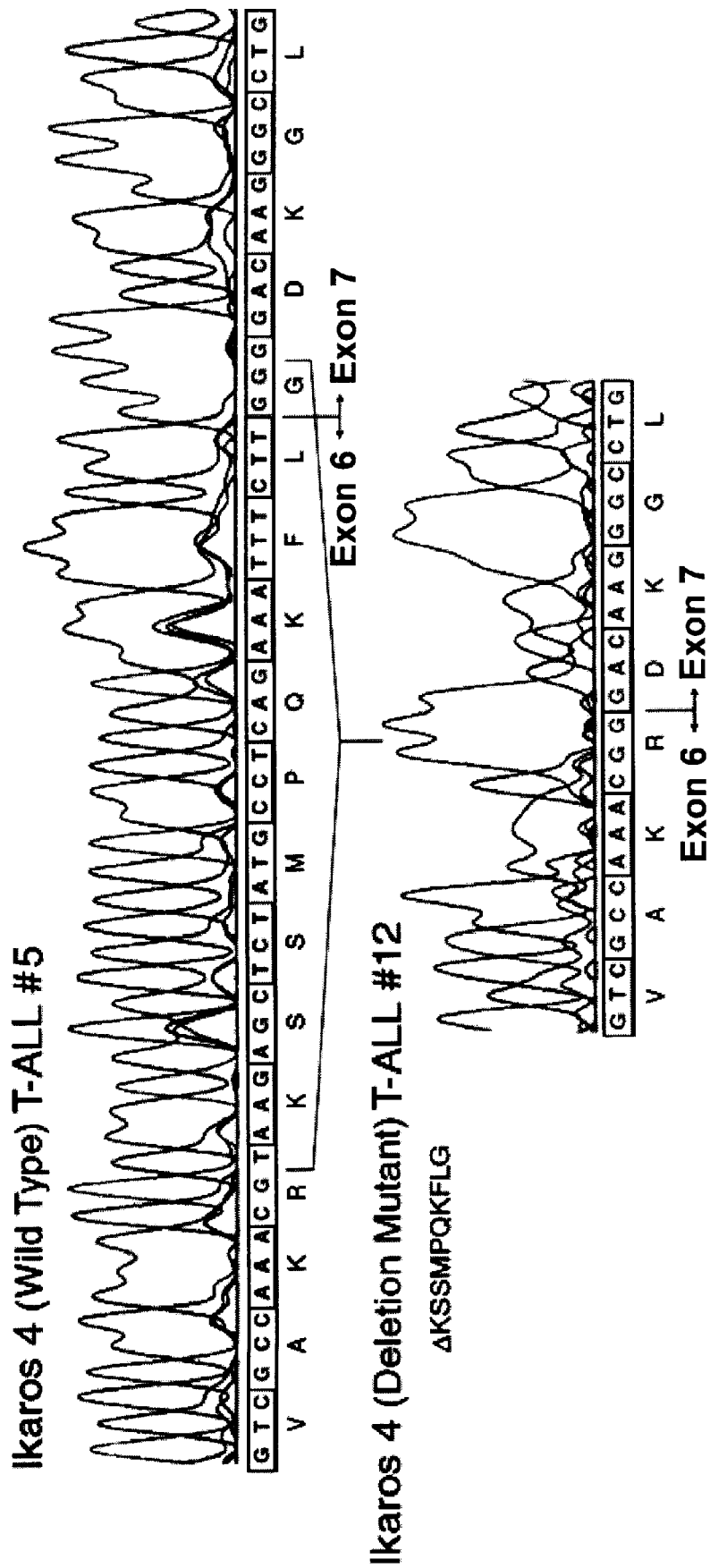
Figure 8C:
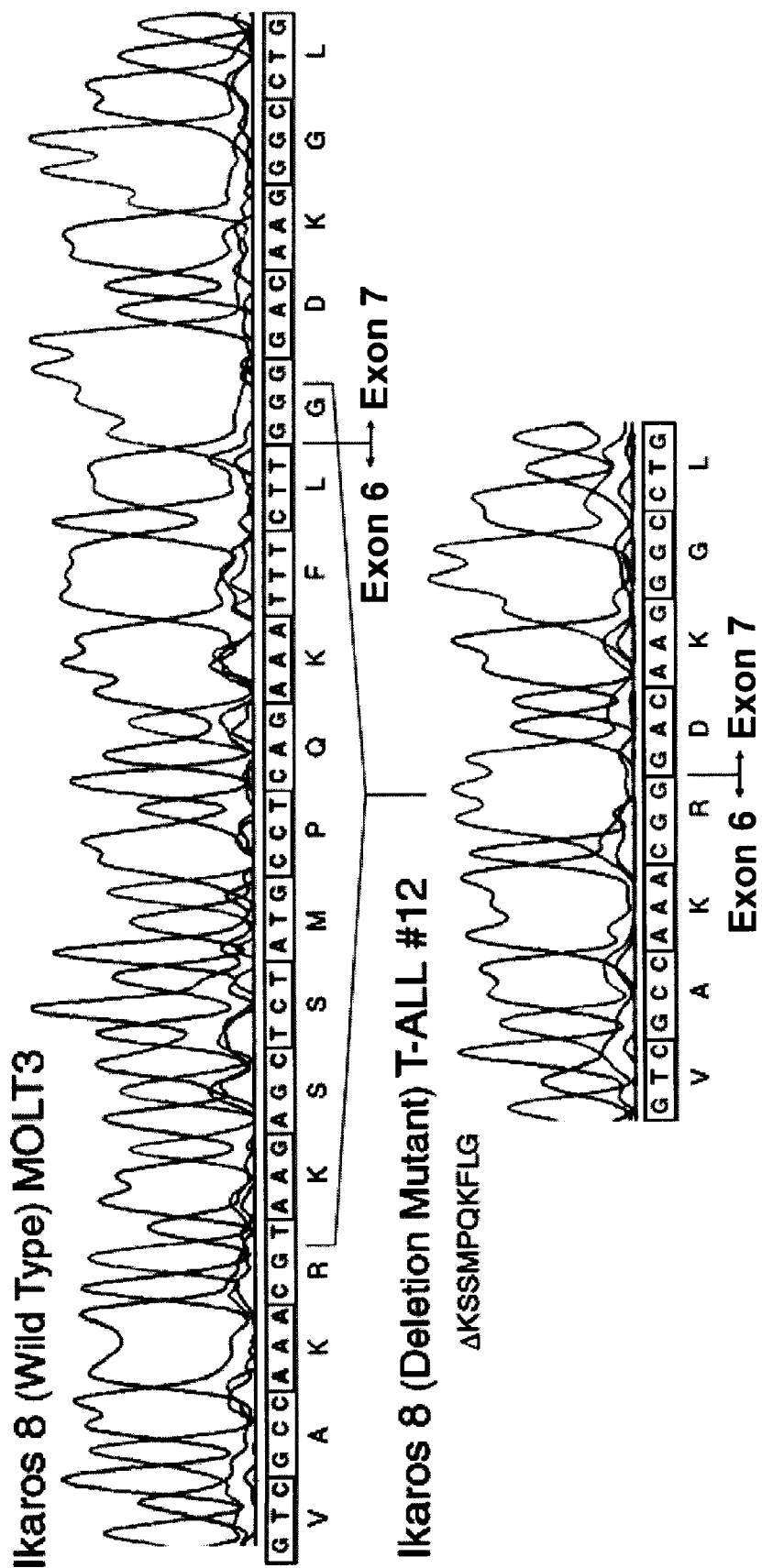
Figure 8D:
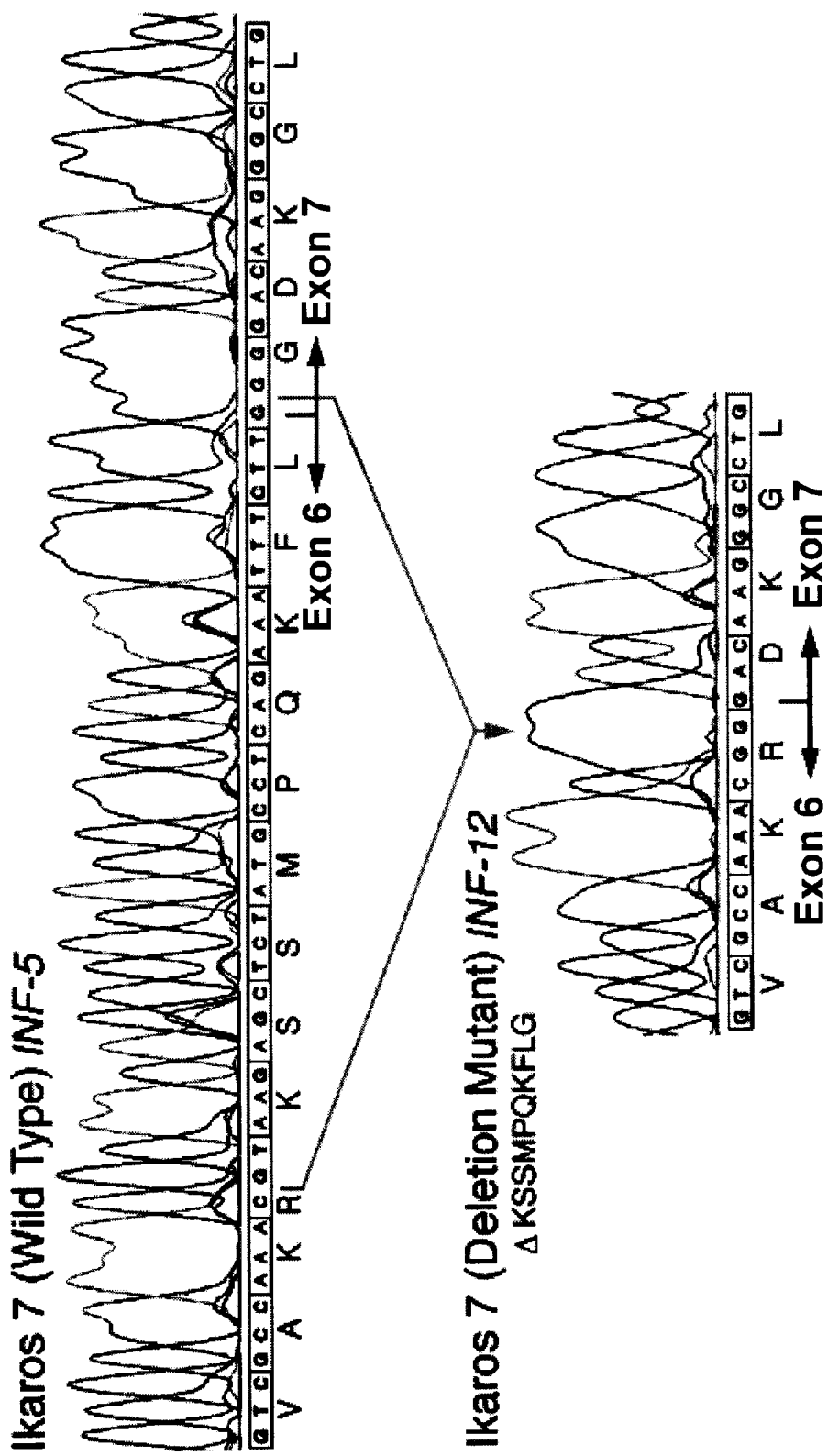
Figure 8E:
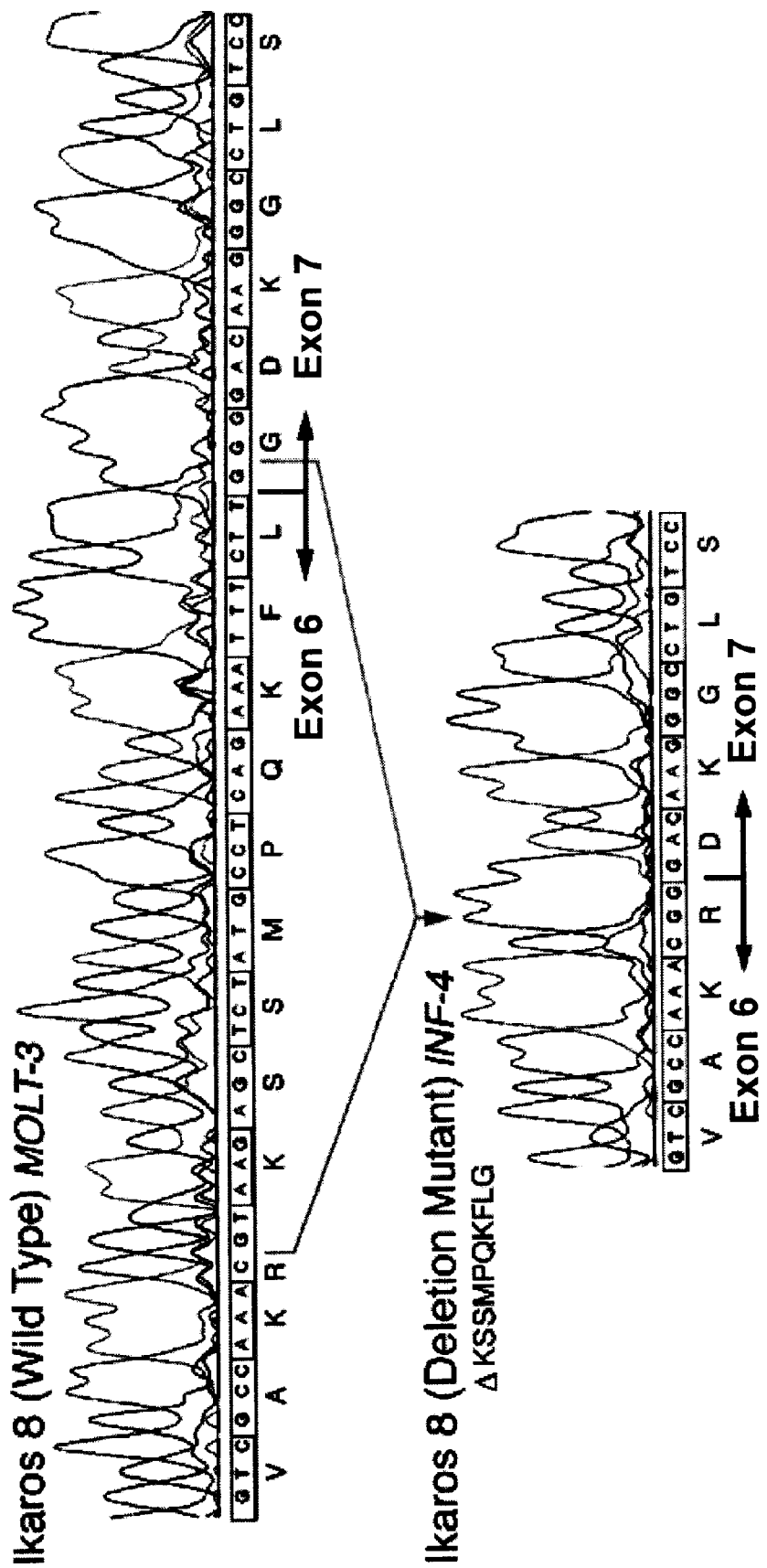
Figure 8F:
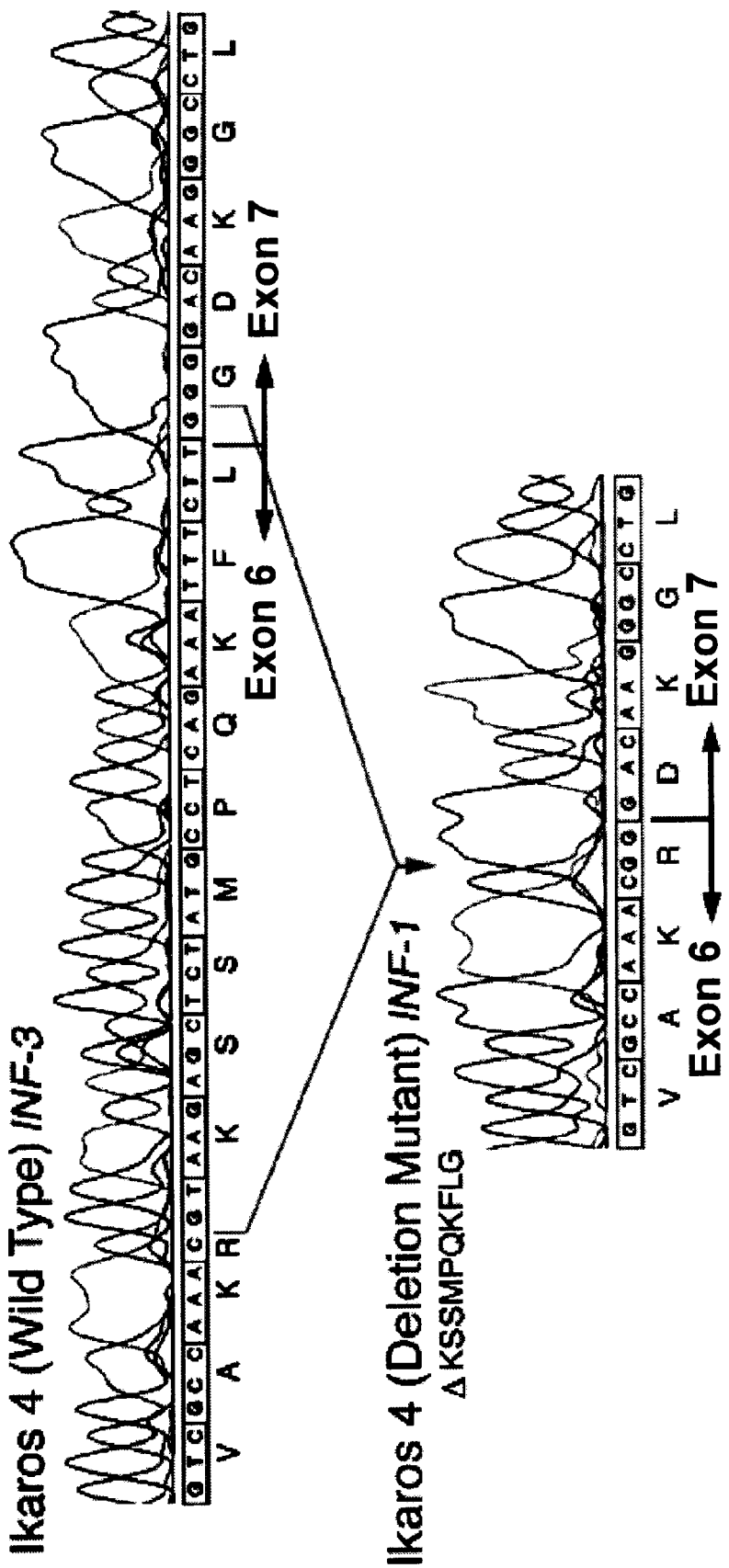

As shown in FIGS. 8A–8C, the resulting deletion mutant exhibited the following mutant sequence:

```
Deletion Mutant: CTC GCC AAA CGG GAC AAG GGC CTG [SEQ ID NO: 26]
                  V   A   K   R   D   K   G   L  [SEQ ID NO: 27]
```

Reactions conducted with RNA isolated from normal fetal thymocytes/infant bone marrow mononuclear cells were used as positive controls for Ikaros transcripts. Negative controls included PCR products from an RNA-free cDNA synthesis and amplification reaction and a DNA polymerase-free reaction.

Purified Ikaros cDNA (QIAquickTM PCR purification kit; Qiagen, Santa Clarita, Calif.) from the nested RT-PCR reaction mixtures was cloned into the pCR II vector using the TA Cloning kit (Invitrogen, San Diego, Calif.). The cloned PCR products were purified with a Qiagen plasmid isolation kit and sequenced automatically with the Thermosequenase sequencing kit (Amersham, Arlington Heights, Ill.) and the ALF Sequencer (Pharmacia, LKB Biotech, Piscataway, N.J.) (Uckun et al., 1991, *Proc. Natl. Acad Sci. USA*, 88:3589–3593). Manual sequencing by the dideoxynucleotide chain termination method was performed using the T7 Sequenase Quick-denature Plasmid Sequencing kit (Amersham) according to the manufacturer's instructions. The sequences were compared with the published human Ikaros cDNA sequence obtained through GenBank (Accession codes S80876 and U40462).

Results

As results of the PCR amplification and sequencing, are shown in FIGS. 5–8. A single PCR amplification product of Leukemic cells from 8 of 10 (80%) T-lineage ALL patients and 5 of 11 (45%) B-lineage ALL patients that were analyzed expressed the non-DNA binding Ikaros isoform Ik-4 (Table 2). Two T-lineage ALL patients expressed only wild-type Ik-4. Two other T-lineage ALL patients expressed wild-type Ik-4 along with wild-type IK2 or the aberrant in-frame 10 amino acid deletion. One T-lineage ALL patient expressed only aberrant Ik-4, having the same 30 bp (10 amino acid) deletion at the 3' end of exon 6, whereas another T-lineage ALL patient and four B-lineage ALL patients expressed this deletion mutant as well as wild-type Ik-1 and/or Ik-2. Two T-lineage ALL patients and one B-lineage ALL patient expressed both wild-type and deletion forms of Ik-4, along with wild-type Ik-1 and/or Ik-2.

In contrast to Ik-4, other dominant-negative isoforms of Ikaros were not frequently expressed in primary leukemic cells from children with ALL: Ik-6 was found in wild-type form in 5 of 5 PCR clones from a single B-lineage ALL patient (Table 2). Ik-7 was found in wild-type form in 2 of 2 PCR clones from a single B-lineage ALL patient and in aberrant form with the exon 2 deletion in at least half of the PCR clones from one T-lineage ALL patient and one B-lineage ALL patient. Ik-8 was found in PCR clones from 3 of 11 B-lineage ALL patients but none of the 10 T-lineage ALL patients (Table 2).

Thus, RT-PCR and sequencing extended the results obtained with confocal microscopy and Western blot analyses, confirming that primary leukemic cells from each child with ALL express small, non-DNA binding wild-type and/or aberrant isoforms of Ikaros. Among 21 cases analyzed, 19 (90.5%) expressed dominant negative Ikaros isoforms, including Ik-4 (12 of 21 patients), Ik-6 (1 of 21 patients), Ik-7 (3 of 21 patients), and Ik-8 (3 of 21 patients). in 15 of 21 cases (71.4%), the PCR clones with coding sequences of Ik-2, Ik-4, Ik-7, and Ik-8 had an identical 30 base pair deletion at the 3' end of exon 6. The observed N-terminal insertions and C-terminal deletions did not cause a frame shift, and therefore did not change the downstream amino acid sequences.

In summary, the expression of non-DNA-binding forms of Ikaros, including isoforms IK 4–8 and mutant forms, such as the 30 amino acid insertion and the 10 amino acid deletion, correlates with lymphoid disease, particularly leukemia.

EXAMPLE 3
Bi-allic and Polymorphic Expression of Ikaros

Expression of aberrant Ikaros isoforms in leukemic cells could result in cis from sequence alterations or from leukemia-associated alterations in trans-acting factors. While cis activation of aberrant expression would cause mono-allelic expression of the aberrant isoforms, transactivation would be more likely to cause bi-allelic expression. The sequence of 128 Ikaros RT-PCR clones from 25 ALL cases were carefully examined for the presence of polymorphic sequence variations by RT-PCR and nucleotide sequence analysis, as described above, to determine whether the aberrant isoforms with the KSSMPQKFLG deletion were mono- or bi-allelically expressed.

Results

Figure 9A:
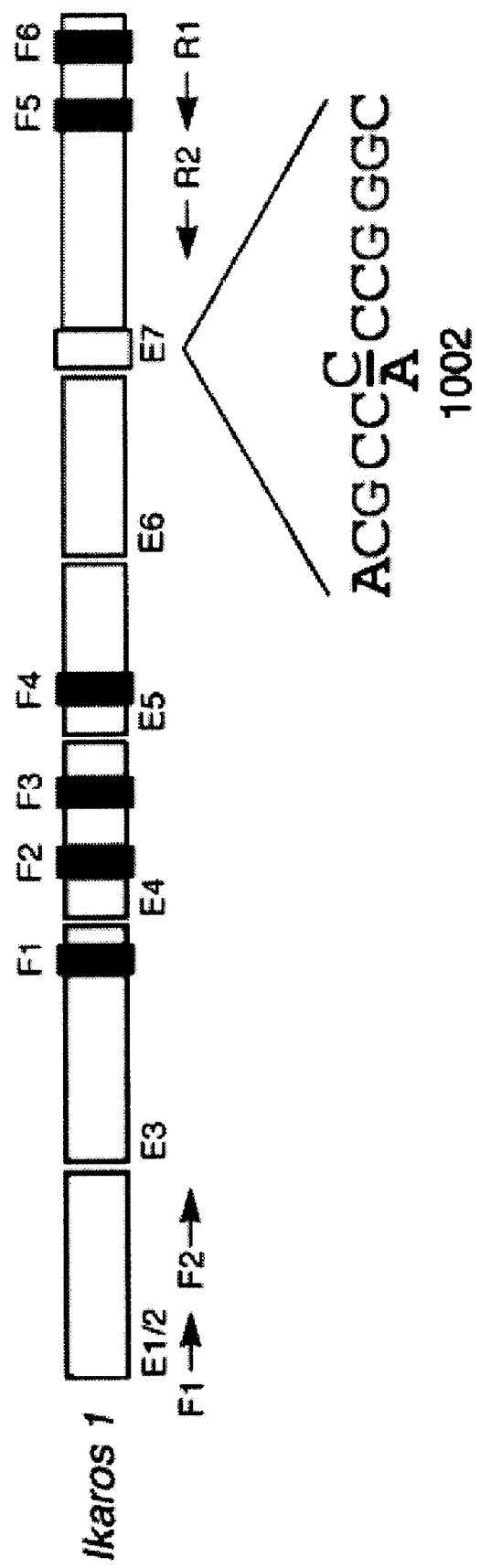
FIGS. 9A and 9B show a single nucleotide polymorphism in Ikaros cDNA and demonstrate bi-allelic expression of normal and aberrant Ikaros isoforms.
Figure 9B:
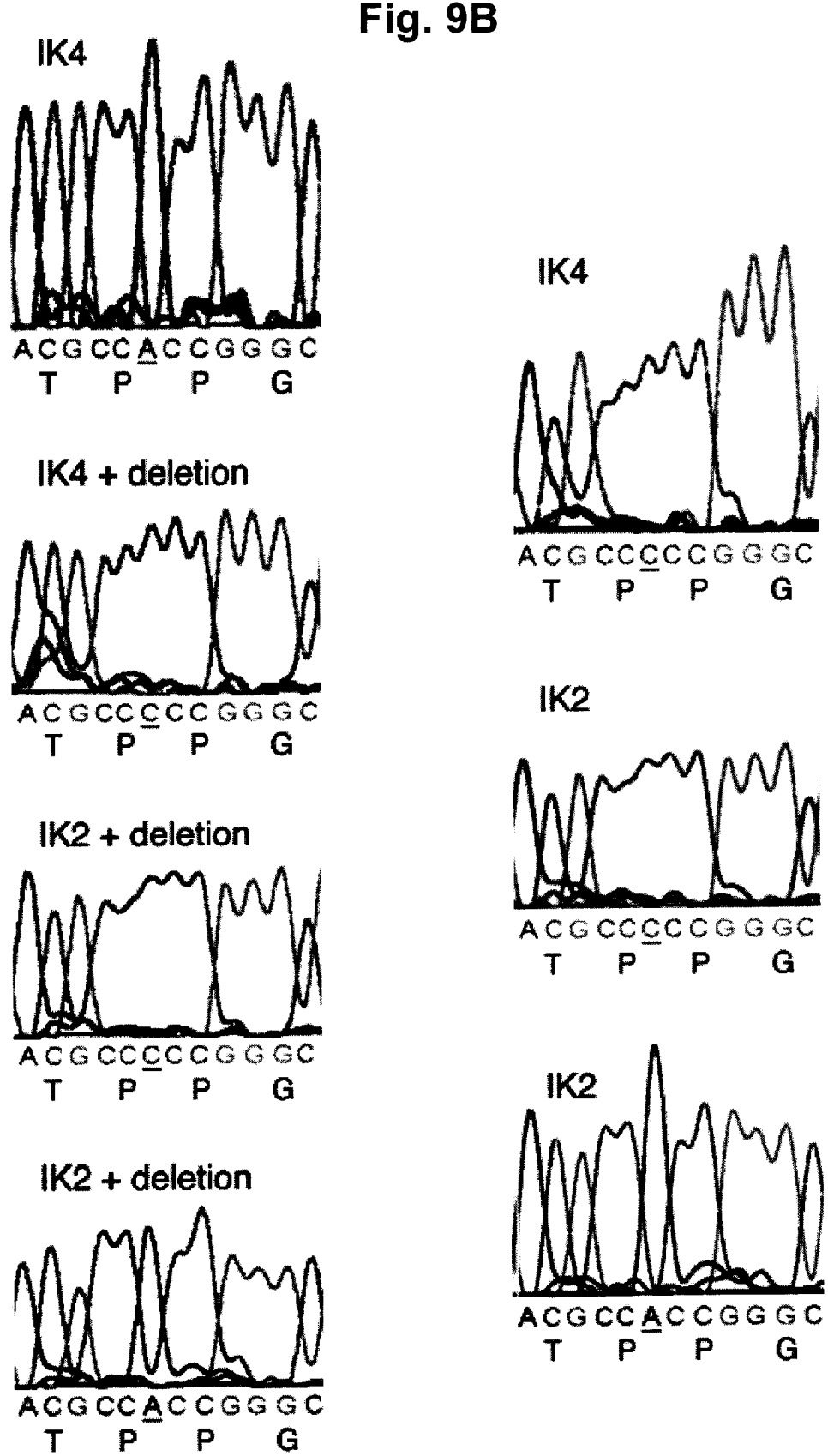

A single nucleotide polymorphism (SNP) within the Ikaros clones at nucleotide position 1002 (numbering from the translational start site of Ik-1-Genbank #U40462 Human Ikaros/LYF-1 homolog (hIK-1) mRNA) was identified as a silent variation affecting the third base of the triplet codon for a proline (CCC or CCA) within exon 7 in the highly conserved bipartite activation region (FIG. 9A). This region is conserved in the various Ikaros splice variants, thereby allowing typing of all Ikaros isoforms. The C allele was observed to be most prevalent (FIG. 9B, Table 3). Similar expression levels of the two polymorphic variant forms (C or A) of Ikaros was observed in 8 of 25 cases, whereas only a single allelic variant (either C, N=15 or A, N=2) was observed in the remaining 17 cases.

Overall, the expression frequencies were 77% (99/128 clones) for the $1002^C$ allele and 23% (29/128 clones) for the $1002^A$ allele. Both allelic variants were observed among wild-type and aberrant Δ KSSMPQKFLG DNA IK 1–3 isoforms as well as in wild-type and aberrant Δ KSSMPQK-FLG IK 4–8 isoforms (FIG. 9B, Table 3). This bi-allelic expression pattern of the various Ikaros isoforms suggest that trans-acting factor(s), possibly affecting splice site recognition, are involved in the generation of the non-DNA binding isoforms (IK 4–8) as well as aberrant (IK (del)) ΔKSSMPQKFLG Ikaros isoforms. Bi-allelic expression was observed during the sequence analysis of aberrant Ikaros Δ KSSMPQKFLG RT-PCR clones from individual patients expressing only the IK-(del) mutants and from patients expressing both IK-(del) mutants and wild-type forms of Ikaros (FIG. 9B). This finding makes it unlikely that the observed deletions could be due to a cis-acting mutation within or surrounding the Ikaros gene. However, an excess of expression of aberrant non-DNA binding isoforms (Δ KSSMPQKFLG) (IK 4–8 (del)) (91% C/9% A) on the C allele, as well as an excess of clones expressing the aberrant DNA binding isoforms (1K 1–3 (del)) on the A allele (42% C/58% A) was observed, suggesting a subtle cis-acting influence on splice site recognition.

TABLE 3

Expression Frequency of Ikaros $1002^A$ and Ikaros $1002^C$ Alleles

| | | 1002 Allele | |
|---|---|---|---|
| PCR Clone | | C | A |
| Ik-1, Ik-2, or Ik-3 | [WT] | 26/33 (79) | 7/33 (21) |
| Ik-1, Ik-2, or Ik-3 | [Δ KSSMPQKFLG] | 8/19 (42) | 11/19 (58) |
| Ik-4, Ik-5, Ik-6, Ik-7, Ik-8 | [WT] | 22/29 (76) | 7/29 (24) |
| Ik-4, Ik-5, Ik-6, Ik-7, Ik-8 | [Δ KSSMPQKFLG] | 43/47 (91) | 4/47 (9) |
| All Clones | | 99/128 (77) | 29/128 (23) |

EXAMPLE 4
Genomic Sequence Analysis of Splice Donor and Acceptor Site Regions

The 10 amino acids involved in the Δ KSSMPQKFLG deletion are encoded at the 3' end of exon 6, upstream of the transcription activation domain. To examine the integrity of the splice donor and acceptor regions in leukemic cells overexpressing the Δ KSSMPQKFLG alternative splice variants of Ikaros, genome walking across the intron-exon junctions between exons 6 and 7 was performed.

Methods

Genomic DNA was isolated from both patient cells and cell lines using the Puregene® DNA isolation kit (Gentra Systems, Inc., Plymouth, Minn.), according to the manufacturer's instructions. The genomic sequence surrounding the predominant splice donor and acceptor sites at the exon-intron splice junction of Ikaros exon 6 was characterized through the use of a GenomeWalker™ Kit (Clontech, Palo Alto, Calif). This kit utilizes very high-quality human placenta genomic DNA which is digested with individual restriction enzymes and then ligated to specifically designed adapters to produce five separate digested DNA "libraries". Amplification of genomic sequence with one unknown end is then possible using one gene-specific primer (P1) and one adapter-specific primer (AP1). Nested PCR amplification with a second gene-specific primer (P2) and a second adapter-specific primer (AP2) followed to produce adequate quantities of region-specific product for use in cloning and sequence analysis. Adaptor-specific primers were provided by the manufacturer. In the first amplification round, the gene-specific PCR primer (P1) from Ikaros exon 6 corresponded to Ikaros sequence +732–+759:

P1a: 5'-TAA TCA CAG TGA ATG GCA GA
  A GAC CTG-3'  [SEQ ID NO: 14];

In the second amplification round, the nested gene-specific Ikaros primer corresponded to Ikaros sequence +747–+774:

P2: 5'-GGC AGA AGA CCT GTG CAA GAT
  AGG ATC A-3'  [SEQ ID NO: 15].

The PCR protocol was performed as recommended in the GenomeWalker™ manual. Briefly, long-range PCR was accomplished with the AdvanTAge® genomic PCR polymerase mix, which is a formulation containing a primary polymerase, Tth; a secondary, proofreading polymerase with 3'→5' exonuclease activity; and TthStart™ antibody, which effectively generates a hot-start PCR. For the first amplification round, the two-step cycling parameters were as follows: 94° C., 25 seconds, 72° C., 4 minutes for 7 cycles; then 94° C., 25 seconds, 67° C. 4 minutes for 32 cycles; followed by a final extension at 67° C. for 4 minutes. In the nested amplification reaction, the cycling parameters were as follows: 94° C. 25 seconds, 72° C. 4 minutes for 5 cycles; 94° C. 25 seconds, 67° C, 4 minutes for 20 cycles; followed by a final extension at 67° C. for 4 minutes.

In the amplification of the 3' splice site, the AdvanTAge® PCR mix was replaced by the Expand™ Long Template PCR system (Roche Molecular Biochemicals), which contains a combination of Taq polymerase and Pwo polymerase, as the proofreading enzyme, along with precise reagent buffer formulations, according to the manufacturer's protocol. Buffer 3, which is formulated for difficult templates and contains detergents, was used at the recommended dilution. In the first amplification round, the gene-specific PCR primer from Ikaros exon 7 (+989–973) was:

P7: 5'-AGC GGG CGC AGG GAC TC-3'     [SEQ ID NO: 16];

The second round, nested primer (+977–957) was:

P6: 5'-GAC TCG GCC CCC AGG TAG TTG-3'[SEQ ID NO: 17].

Adapter specific primer AP1 and AP2, provided by the manufacturer, were used as above. AP1 was used in the first round of PCR amplification, and primer AP2, described above, was used in the second round of nested PCR amplification.

The PCR protocol was performed essentially as recommended in the GenomeWalker™ manual and as described above. Human tissue-type plasminogen activator (tPA) PCR primers were the positive control primers (PCP 1, PCP2) and were provided with the GenomeWalker kit. The tPA control cycling parameters were as described in the manufacturer's protocol using the genomic library digest, PvuII.

Nested PCR products were cloned using the TOPO™ TA Cloning® Kit (Invitrogen, Carlsbad, Calif.). Plasmid minipreps of the cloned DNA were performed using the High Pure™ Plasmid Isolation Kit (Roche Molecular Biochemicals, Indianapolis, Id.). Clones containing insert were sequenced using a Thermo Sequenase™ primer cycle sequencing kit (Amersham Pharmacia Biotech, Piscataway, N.J.) and the ALFexpress automated DNA sequencer (Amersham Pharmacia). In the amplification of the 3' splice junction, DMSO was added to the cycle sequencing reactions at a final concentration of 5% v/v. Ikaros cDNAs of GenBank accession nos. HSU40462 (human Ikaros mRNA, hIk-1 [SEQ ID NO: 18]) and S80876 (human Ikaros mRNA, alternatively spliced form, Jurkat [SEQ ID NO: 19]) were used in sequence comparisons and mapping.

Sequence obtained using the GenomeWalker™ kit was used to design primers to directly amplify the region surrounding the 5' splice junction of Ikaros exons 6 and 7 from the patient and cell line genomic DNA. For the 5' splice site, PCR was carried out using two primer sets which differ in the placement of the intronic (anti-sense) primer to amplify fragments of 342 bp and 211 bp. The sense primers from exon 6 used to amplify both products were:

P1a: 5'-TAA TCA CAG TGA ATG
     GCA GAA GAC CTG-3'     [SEQ ID NO: 14] (+732–759);

or

P1b: 5'-TAA GCA CAG TGA AAT
     GGC AGA AGA CCT G-3'     [SEQ ID NO: 20] (+732–759).

The sequence of the anti-sense primers used to amplify two fragments of different lengths, 342 and 211 bp, were:

P4: 5'-ATG CTG CAA AAT CAA
    ATC TAG GAA AAA C-3'     [SEQ ID NO: 21] (+223–196);

and

P3: 5'-TTT CCC TTT CTT CCA CCC
    TCA ACT CAT-3'     [SEQ ID NO: 22] (+92–65), respectively.

PCR was performed using 500 ng of genomic DNA in a 50 μl reaction volume using the Expand™ Long Template PCR system (Roche Molecular Biochemicals) with buffer and component concentrations, as recommended by the GenomeWalker™ kit manufacturer, using buffer system 3 for difficult templates. The long-range PCR cycling parameters were as follows: 95° C. for 2 minutes (complete denaturation) which is followed by 10 cycles at 94° C. for 25 seconds, 65° C. for 30 seconds, extension at 68° C. for 2 minutes; with an additional 20 cycles of 94° C. for 25 seconds, 65° C. for 30 seconds, 68° C. for 2 minutes (extension) in which 20 seconds is added per cycle to the extension step, and then a final extension at 68° C. for 10 minutes.

The resulting products were cloned using the TOPO™ TA Cloning® Kit (Invitrogen). Plasmid minipreps of the cloned DNA were performed using the High Pure™ Plasmid Isolation Kit (Roche Molecular Biochemicals, Indianapolis, Ind.). Clones containing insert were sequenced using the Thermo Sequenase™ primer cycle sequencing kit (Amersham Pharmacia, Piscataway, N.J.) and an ALFexpress automated sequencer (Amersham Pharmacia).

For the 3' splice site, genomic PCR was performed as above with the Expand™ Long Template PCR system (Roche Molecular Biochemicals), but using buffer system 1 and 5% v/v DMSO. The sense primer for the 3' splice site was P5, having an intronic position of −244 to −223 from the splice acceptor site, and the anti-sense primer was P6, having a cDNA position of +977 to +957.

P5: 5-GTA GGT CCT GGC TCG GTG TCC C-3[SEQ ID NO: 23]
    (intronic position −244 to −223 from the splice acceptor site);

and

P6: 5'-GAC TCG GCC CCC AGG TAG TTG-3
    [SEQ ID NO: 17] (position in cDNA +977–957).

In this case, the long-range PCR cycling parameters were 1×95° C., 3 minutes; 10×95° C., 30 seconds, 66° C., 45 seconds, 68° C., 2 minutes, 68° C, 2 minutes; 20×95° C., 30 seconds, 66° C., 45 seconds, 68° C., 2 minutes+10 seconds/cycle; 1×68° C., 5 minutes. For this 3' fragment analysis, DMSO was added to both the genomic PCR and the cycle sequencing reactions at a final concentration of 5% v/v.

Results

Figure 10A:
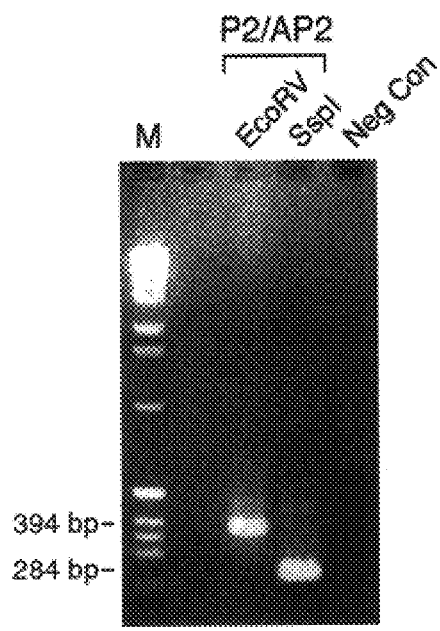

Genome walking across the intron-exon junctions between exons 6 and 7 yielded the wild-type sequence. For analysis of the 5' splice site, single bands were successfully obtained as a result of nested PCR from two out of five genomic DNA libraries (EcoRV and SspI) provided with the GenomeWalker™ kit (FIG. 10A). Four clones from each of these libraries were chosen for sequence analysis. Results from this initial sequence comparison (FIG. 11A) showed a complete match to the 3' end of exon 6 from the Ikaros mRNA (accession no. U40462, 100% consensus).

FIGS. 10A–10E show photographs of representative ethidium bromide stained gels revealing PCR products used to determine sequence covering the exon 6/7 splice junction. FIG. 10A shows the nested PCR products generated by amplification of the exon 6 donor site region with the GenomeWalker™ kit using the gene-specific primer, P2, and the GenomeWalker™ adapter primer, AP2, to amplify restriction enzyme (EcoRV or SspI) digested, adapter-ligated genomic DNA.

Figure 10B:
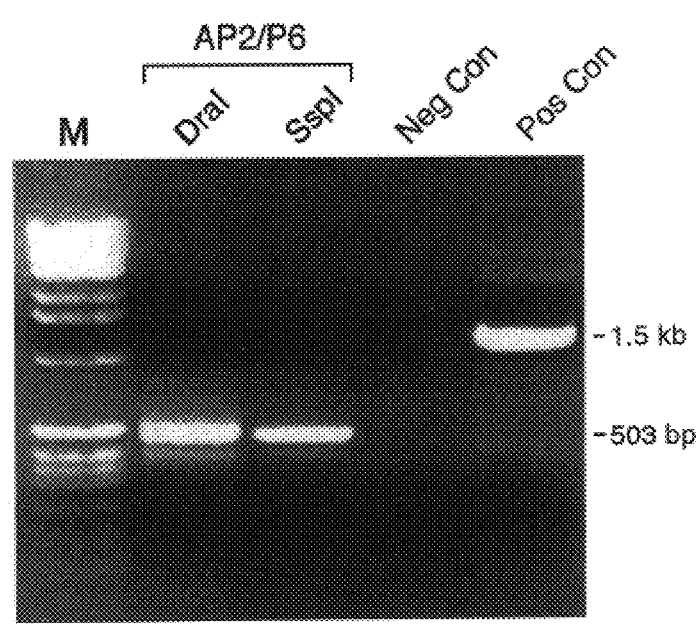

FIG. 10B shows the nested PCR product surrounding the exon 7 slice acceptor site obtained by amplification of DraI or SspI digested adapter-ligated genomic DNA with the AP2 and gene-specific primer 6, P6.

FIG. 10C shows genomic PCR amplification products, using primer sets [P1a and P4] or [P1b and P4], for the exon 6 donor site obtained from control cells (LCL, EBV-transformed B-lymphoblatoid control cell line), leukemic cell lines (Jurkat, Molt-3), and primary leukemic cells from patients (UPN 1 amd UPN 2).

FIG. 10D shows genomic PCR amplification products for the exon 6 donor site obtained from control cells and primary leukemic cells from patients, amplified using primer set P1b and P3.

FIG. 10E shows genomic PCR amplification products for the exon 7 acceptor site obtained from control cells and primary leukemic cells from patients, amplified using primer set P5 (SEQ ID NO: 23) and P6 (SEQ ID NO: 17). Molecular weight markers (M): 1 kb DNA ladder. Negative control (Neg. Con.) was duplicate reactions without template (either library digest or genomic DNA sample). Positive control (Pos. Con.) was tissue-type plasminogen activator (tPA), nested primer set, AP2 and PCP2, with a predicted band at 1.5 kb. Two hundred fifty four base pairs of novel genomic sequence into the intron adjacent to to the 5' end of exon 6 were characterized [SEQ ID NO: 24].

For the 3' splice site, two out of five genomic DNA libraries (DraI and SspI) provided with the GenomeWalker™ kit successfully produced single bands (503 bp from both libraries) as a result of nested PCR (FIG. 10B). An average of four clones from each library were chosen for sequence analysis. Again, a complete match was obtained to the Ikaros mRNA (accession no. U40462) across exon 7 sequence (FIG. 12A). For this region, 340 base pairs of novel intron sequence upstream from exon 7 was characterized [SEQ ID NO: 25]. This sequence was then used to develop primers to directly amplify this region of the splice junction and intronic sequence from genomic DNA of patients and cell lines.

Subsequent amplification and genomic sequence analysis of the corresponding exon 6- exon 7 splice junction regions from leukemic patients and cell lines expressing the deletion variant demonstrated no mutation in the region spanning the cryptic splice site, as well as at the predominant 5' (donor) or 3' (acceptor) splice sites. Bands of the predicted sizes were obtained by genomic PCR of DNA from the patients and cell lines of those samples expressing the alternative splice variant. FIGS. 10C and 10D show data for the 5' splice site. FIG. 10E shows data for the 3' splice site. No size differences were detected by restriction analysis of numerous cloned isolates covering both the 5' and 3' splice sites.

Figure 11A:
FIGS. 11A–11B depict the genomic sequence of Ikaros exon 6 splice donor site in leukemic patients expressing the exon 6 deletion.
Figure 11B:
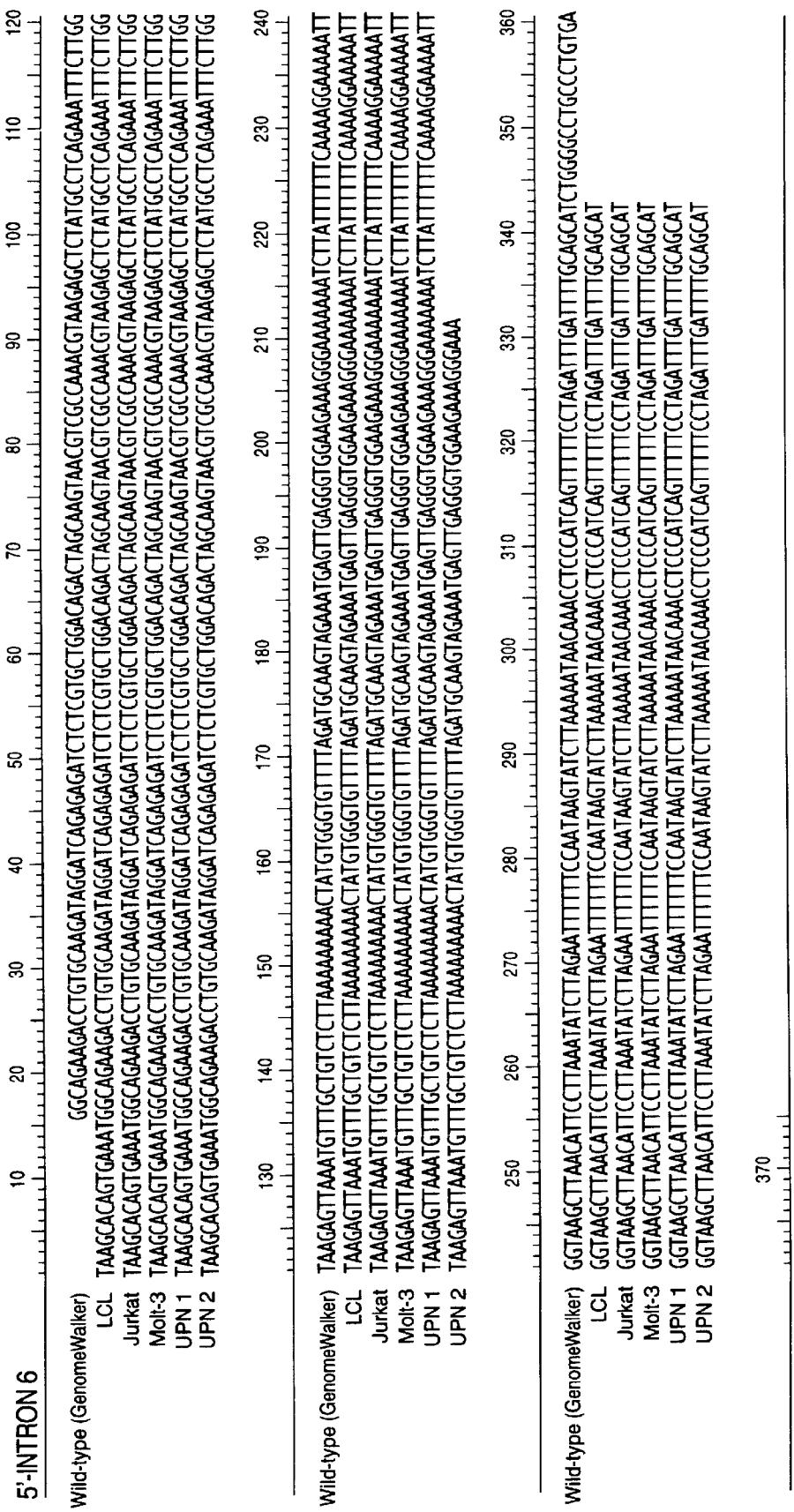

A minimum of six clones from each sample were sequenced for mutational analysis. Sequencing results confirmed the presence of the region between the alternative splice sites in all genomic DNAs examined. There was no mutation within a 284 base pair sequence at the normal splice donor site or the region directly surrounding the deleted sequence, i.e., near the cryptic splice donor site (FIGS. 11A and 11B). Similarly, no mutations were found within a 328 base pair sequence at the 3' splice acceptor site (FIG. 12).

In summary, these data demonstrate conservation and integrity of the splice donor and acceptor regions across the intron-exon junctions between exons 6 and 7 in leukemic cells expressing the IK-deletion alternative splice variants.

All publications and patent applications recited in this specification are indicative of the level of ordinary skill in the art to which this invention pertains. All publications and patent applications are herein incorporated by reference to the same extent as if each individual publication or patent application was specifically and individually indicated by the reference.

| ID NO: | SEQUENCE |
|---|---|
| 1. | GGGAAT |
| 2. | TCAGCTTTTGGGAATACCCTGTCA |
| 3. | TCAGCTTTTGGGggTACCCTGTCA |
| 4. | ATGGATGCTGACGAGGGTCAAGAC |
| 5. | TTAGCTCATGTGGAAGCGGTGCTC |
| 6. | CTCATCAGGGAAGGAAAGCC |
| 7. | GGTGTACATGACGTGATCCAGG |
| 8. | TTCAGCGGCCAGTAGCATCTGACTT |
| 9. | TGTGATTATAGCCTAAGACCCGGAG |
| 10. | GTT ACA TAT GGG GCT GAT GAC TTT AGG GAT TTC CAT GCA ATA ATT CCC AAA TCT TTC TCT CGA |
| 11. | VTYGADDFRDFHAIIPKSFS R |
| 12. | T AAG AGC TCT ATG CCT CAG AAA TTT CTT GG |
| 13. | K S SM PQKFLG |
| 14. | TAA TCA CAG TGA ATG GCA GAA GAC CTG |
| 15. | GGC AGA AGA CCT GTG CAA GAT AGG ATC A |
| 16. | AGC GGG CGC AGG GAC TC |
| 17. | GAC TCG GCC CCC AGG TAG TTG |
| 18. | HSU40462 |
| 19. | S80876 |
| 20. | TAA GCA CAG TGA AAT GGC AGA AGA CCT G |
| 21. | ATG CTG CAA AAT CAA ATC TAG GAA AAA C |
| 22. | TTT CCC TTT CTT CCA CCC TCA ACT CAT |
| 23. | GTA GGT CCT GGC TCG GTG TCC C |
| 24. | ATTAAATGAAATACAATAACATAATTAAACTAATCTTTGGTTCC CCTATTTATGTATTCATTTATCCAACAAAATCTCCTTAAGTGCT TATAATGGGTAGGTCCTGGCTCGGTGTCCCCTAGACAGACGCAT GGGCCTTCCCCCAGCCCGTCAGTATGGTGCAGGTGTGATGTGTC CGCAGGTGTGTGTGTATGTGTGCAGGTGTGGGGTCCGCAGGCGT GCTGGGCCCCCAGGCCGTGTTCCCCTTCCCCTCCCCGGTTGTAG ATTTCAGCTGTTGCTGCCAGACCTGACCGGTTCCGGAGGTGGCC GCGCCCCACTCACTGTCGCCTGCTTTCCACAGGGGACAAGGGCC TGTCCGACACGCCCTACGACAGCAGCGCCAGCTACGAGAAGGAG AACGAAATGATGAAGTCCCACGTGATGGACCAAGCCATCAACAA CGCCATCAACTACCTGGGGGCCGAGTC |
| 25. | TAAGCACAGTGAAATGGCAGAAGACCTGTGCAAGATAGGATCAG AGAGATCTCTCGTGCTGGACAGACTAGCAAGTAACGTCGCCAAA CGTAAGAGCTCTATGCCTCAGAAATTTCTTGGTAAGAGTTAAAT GTTTGCTGTCTCTTAAAAAAAAACTATGTGGGTGTTTTAGATGC AAGTAGAAATGAGTTGAGGGTGGAAGAAAGGGAAAAAAATCTTA TTTTTTCAAAAGGAAAAATTGGTAAGCTTAACATTCCTTAAATA TCTTAGAATTTTTTCCAATAAGTATCTTAAAAATAACAAACCTC CCATCAGTTTTTCCTAGATTTGATTTTGCAGCATCTGGGGCCTG CCCTGTGATCTGCCTGTGGAC |
| 26. | CTC GCC AAA CGG GAC AAG GGC CTG |
| 27. | V A K R D K G L |

We claim:

1. A method for the detection of abnormal lymphohematopoietic cells, comprising analyzing a sample of lymphoid cells for the presence of Ikaros isoforms encoded at least in part by exons 6–7 and lacking the following Ikaros amino acid sequence: KSSMPQKFLG (SEQ ID NO: 13).

2. A method for the detection of abnormal lymphohematopoietic cells, comprising analyzing a sample of lymphoid cells for the presence of Ikaros isoforms having an insertion of the following amino acid sequence: VTYGADDFRDFHAIIPKSFSR (SEQ ID NO: 11).

3. A method for the detection of hematologic malignancy, the method comprising: a) analyzing a sample of hematologic cells for expression of mutant Ikaros isoforms and, b) correlating the expression of the mutant protein isoforms with hematologic malignancy, wherein said malignancy is non-Hodgkin's lymphoma.

4. A method for the detection of hematologic malignancy, the method comprising: a) analyzing a sample of hematologic cells for expression of mutant Ikaros isoforms and, b) correlating the expression of the mutant protein isoforms with hematologic malignancy, wherein said malignancy is Hodgkin's lymphoma.

* * * * *

UNITED STATES PATENT AND TRADEMARK OFFICE
CERTIFICATE OF CORRECTION

PATENT NO.    : 6,537,766 B1
DATED         : March 25, 2003
INVENTOR(S)   : Uckun et al.

It is certified that error appears in the above-identified patent and that said Letters Patent is hereby corrected as shown below:

<u>Title page,</u>
Item [56], References Cited, U.S. PATENT DOCUMENTS, insert
-- 4,816,567    03/1989    Cabilly et al. --
OTHER PUBLICATIONS,
"Sun, L. et al." reference, "XP-00086468" should read -- XP-000864668 --
"Chessells, J.M. et al." reference, (two occurrences) "Leukaemia" should
read -- Leukemia --
"Luo, Z., et al." reference, "Spicing" should read -- Splicing --
After the "Reaman, G. et al." reference, insert -- Rowley, J., "Backtracking Leukemia to Birth," *Nature Medicine*, Vol. 4, No. 2, pp. 150-151 (February 1998). --

<u>Column 2,</u>
Line 15, "identifed," should read -- identified, --
Line 40, "hematoloic" should read -- hematologic --
Lines 49-50, "there-apeutic" should read -- therapeutic --

<u>Column 3,</u>
Line 57, "interraction" should read -- interaction --

<u>Column 5,</u>
Line 24, "Regulaton" should read -- Regulation --

<u>Column 6,</u>
Line 20, "diseasedt" should read -- diseased --

<u>Column 8,</u>
Lines 1 and 2, "lcancer and with ymphoid" should read -- cancer and with lymphoid --
Line 6, "lymphhoid" should read -- lymphoid --

<u>Column 10,</u>
Lines 46-47, "B-lineage All subgroup included 30 infants (<12 months of age) with all and 11 children with high risk ALL." should read -- B-lineage ALL subgroup included 30 infants (<12 months of age) with ALL and 11 children with high risk ALL. --

UNITED STATES PATENT AND TRADEMARK OFFICE
CERTIFICATE OF CORRECTION

PATENT NO. : 6,537,766 B1
DATED : March 25, 2003
INVENTOR(S) : Uckun et al.

It is certified that error appears in the above-identified patent and that said Letters Patent is hereby corrected as shown below:

Column 11,
Line 42, "1C and G) primarily" should read -- 1C) primarily --

Column 17,
Line 7, "in 15" should read -- Furthermore, in 15 --

Column 21,
Line 25, "adjacent to to the" should read -- adjacent to the --

Signed and Sealed this

Twenty-second Day of July, 2003

JAMES E. ROGAN
*Director of the United States Patent and Trademark Office*